(12) United States Patent
Clavelle et al.

(10) Patent No.: US 11,504,057 B2
(45) Date of Patent: Nov. 22, 2022

(54) OPTICAL SENSOR SUBSYSTEM ADJACENT A COVER OF AN ELECTRONIC DEVICE HOUSING

(71) Applicant: Apple Inc., Cupertino, CA (US)

(72) Inventors: Adam T. Clavelle, San Francisco, CA (US); Tobias J. Harrison-Noonan, San Francisco, CA (US); Erik G. de Jong, San Francisco, CA (US); Ueyn L. Block, Menlo Park, CA (US)

(73) Assignee: Apple Inc., Cupertino, CA (US)

( * ) Notice: Subject to any disclaimer, the term of this patent is extended or adjusted under 35 U.S.C. 154(b) by 466 days.

(21) Appl. No.: 16/118,254

(22) Filed: Aug. 30, 2018

(65) Prior Publication Data
US 2019/0090806 A1   Mar. 28, 2019

Related U.S. Application Data

(60) Provisional application No. 62/563,529, filed on Sep. 26, 2017.

(51) Int. Cl.
*A61B 5/00* (2006.01)
*A61B 5/024* (2006.01)
(Continued)

(52) U.S. Cl.
CPC .......... *A61B 5/681* (2013.01); *A61B 5/02427* (2013.01); *A61B 5/02438* (2013.01);
(Continued)

(58) Field of Classification Search
CPC ....... A61B 5/681; A61B 5/25; A61B 5/02427; A61B 5/02438; A61B 5/1544;
(Continued)

(56) References Cited

U.S. PATENT DOCUMENTS

| 4,015,595 A * | 4/1977 | Benjamin, Jr. | .... A61B 5/02427 600/479 |
| 6,198,951 B1 * | 3/2001 | Kosuda | .............. A61B 5/02416 600/323 |

(Continued)

FOREIGN PATENT DOCUMENTS

| CN | 1572252 | 2/2005 |
| CN | 1985762 | 6/2007 |

(Continued)

OTHER PUBLICATIONS

Invitation to Pay Additional Fees dated Feb. 1, 2019, PCT/US2018/048961, 14 pages.

(Continued)

*Primary Examiner* — Amanda Lauritzen Moher
*Assistant Examiner* — Brooke Lyn Klein
(74) *Attorney, Agent, or Firm* — Brownstein Hyatt Farber Schreck, LLP

(57) ABSTRACT

A watch having a cover is described. An optical sensor subsystem is attached adjacent to or directly on an interior surface of the cover. In some cases, the optical sensor subsystem includes a substrate to which a light emitter and a light receiver are attached. The light receiver is configured to receive light emitted by the light emitter and reflected from the skin of a person that wears the watch. In some cases, the light emitter and light receiver are separated by a light-blocking wall that abuts the interior surface of the cover. In some cases, a light filter is attached adjacent or directly on the interior surface of the cover, between the cover and the light receiver.

20 Claims, 15 Drawing Sheets

(51) Int. Cl.
  *A61B 5/25* (2021.01)
  *G04G 9/00* (2006.01)
  *G04G 21/02* (2010.01)
  *A61B 5/1455* (2006.01)

(52) U.S. Cl.
  CPC ............. *A61B 5/25* (2021.01); *G04G 9/0088* (2013.01); *G04G 21/025* (2013.01); *A61B 5/1455* (2013.01); *A61B 5/743* (2013.01); *A61B 5/7475* (2013.01); *A61B 2560/0468* (2013.01); *A61B 2562/0238* (2013.01); *A61B 2562/185* (2013.01)

(58) Field of Classification Search
  CPC .................. A61B 5/743; A61B 5/7475; A61B 2560/0468; A61B 2562/0238; A61B 2562/185; G04G 9/0088; G04G 21/025
  See application file for complete search history.

(56) References Cited

U.S. PATENT DOCUMENTS

| | | | |
|---|---|---|---|
| 6,428,537 B1* | 8/2002 | Swanson | A61B 18/1492 606/41 |
| 6,608,562 B1* | 8/2003 | Kimura | A61B 5/02427 128/903 |
| 6,996,428 B2 | 2/2006 | Kislov et al. | |
| 7,450,002 B2 | 11/2008 | Choi et al. | |
| 7,486,386 B1 | 2/2009 | Holcombe | |
| 7,729,748 B2 | 6/2010 | Florian | |
| 7,822,469 B2 | 10/2010 | Lo | |
| 7,894,888 B2 | 2/2011 | Chan et al. | |
| 7,915,601 B2 | 3/2011 | Setlak et al. | |
| 7,957,762 B2 | 6/2011 | Herz et al. | |
| 8,758,258 B2 | 6/2014 | Takahashi et al. | |
| 8,842,848 B2 | 9/2014 | Donaldson et al. | |
| 8,954,135 B2 | 2/2015 | Yuen et al. | |
| 8,988,372 B2 | 3/2015 | Messerschmidt et al. | |
| 9,042,971 B2 | 5/2015 | Brumback et al. | |
| 9,100,579 B2 | 8/2015 | Schatvet et al. | |
| 9,348,322 B2 | 5/2016 | Fraser et al. | |
| 9,427,191 B2 | 8/2016 | LeBoeuf | |
| 9,442,570 B2 | 9/2016 | Slonneger | |
| 9,485,345 B2 | 11/2016 | Dantu | |
| 9,506,802 B2 | 11/2016 | Chu et al. | |
| 9,516,442 B1 | 12/2016 | Dusan | |
| 9,557,716 B1 | 1/2017 | Inamdar | |
| 9,620,312 B2 | 4/2017 | Ely et al. | |
| 9,627,163 B2 | 4/2017 | Ely et al. | |
| 9,687,165 B2 | 6/2017 | Katra et al. | |
| 9,715,301 B2 | 7/2017 | Kuboyama et al. | |
| 9,723,997 B1 | 8/2017 | Lamego | |
| 9,737,221 B2 | 8/2017 | Sato | |
| 9,772,605 B2 | 9/2017 | Shim et al. | |
| 9,833,159 B2 | 12/2017 | Chu et al. | |
| 9,848,823 B2 | 12/2017 | Raghuram et al. | |
| 9,971,399 B2 | 5/2018 | Lee | |
| 10,013,075 B2 | 7/2018 | Shipman | |
| 10,058,773 B2 | 8/2018 | Huang | |
| 10,123,710 B2 | 11/2018 | Gassoway et al. | |
| 10,126,194 B2 | 11/2018 | Lee | |
| 10,271,800 B2 | 4/2019 | Lin et al. | |
| 10,488,936 B2 | 11/2019 | Baranski | |
| 10,524,720 B2 | 1/2020 | Newberry | |
| 10,551,929 B2 | 2/2020 | Kim | |
| 2002/0151775 A1* | 10/2002 | Kondo | G04G 21/025 600/344 |
| 2003/0045802 A1* | 3/2003 | Kato | A61B 5/681 600/503 |
| 2004/0000713 A1* | 1/2004 | Yamashita | H01L 35/32 257/728 |
| 2005/0116820 A1* | 6/2005 | Goldreich | A61B 5/681 340/539.12 |
| 2006/0069319 A1 | 3/2006 | Elhag et al. | |
| 2009/0265671 A1* | 10/2009 | Sachs et al. | |
| 2011/0004106 A1* | 1/2011 | Iwamiya | A61B 5/02427 600/476 |
| 2011/0015496 A1 | 1/2011 | Sherman et al. | |
| 2013/0310656 A1 | 11/2013 | Lim | |
| 2014/0070081 A1* | 3/2014 | Spraggs | G01J 1/0271 250/221 |
| 2014/0073486 A1 | 3/2014 | Ahmed et al. | |
| 2014/0275832 A1 | 9/2014 | Muehlsteff et al. | |
| 2015/0002088 A1* | 1/2015 | D'Agostino | H02J 7/0044 320/108 |
| 2015/0270058 A1* | 9/2015 | Golko | H01F 38/14 307/104 |
| 2015/0355604 A1* | 12/2015 | Fraser | A61B 5/14552 368/10 |
| 2016/0058309 A1 | 3/2016 | Han | |
| 2016/0058375 A1* | 3/2016 | Rothkopf | A61B 5/0205 600/301 |
| 2016/0103985 A1* | 4/2016 | Shim | A61B 5/02427 726/19 |
| 2016/0120472 A1 | 5/2016 | Kub et al. | |
| 2016/0198966 A1 | 7/2016 | Uernatsu et al. | |
| 2016/0240721 A1* | 8/2016 | Chu | G01J 1/0437 |
| 2016/0242659 A1 | 8/2016 | Yamashita et al. | |
| 2016/0338598 A1 | 11/2016 | Kegasawa | |
| 2016/0338642 A1 | 11/2016 | Parara et al. | |
| 2016/0345881 A1* | 12/2016 | Sarantos | A61B 5/02438 |
| 2016/0349803 A1 | 12/2016 | Dusan | |
| 2016/0378071 A1 | 12/2016 | Rothkopf | |
| 2017/0011210 A1 | 1/2017 | Cheong et al. | |
| 2017/0049332 A1 | 2/2017 | Park et al. | |
| 2017/0086692 A1* | 3/2017 | Freschi | A61B 5/02438 |
| 2017/0090599 A1 | 3/2017 | Kuboyama et al. | |
| 2017/0181644 A1 | 6/2017 | Meer et al. | |
| 2017/0230754 A1 | 8/2017 | Dusan | |
| 2017/0296088 A1* | 10/2017 | Choi | A61B 5/7271 |
| 2017/0354332 A1 | 12/2017 | Lamego | |
| 2018/0020937 A1 | 1/2018 | Chou | |
| 2018/0220972 A1 | 8/2018 | Jeong | |
| 2018/0235483 A1* | 8/2018 | Mouradian | G04G 21/00 |
| 2018/0235542 A1 | 8/2018 | Yun et al. | |
| 2019/0025438 A1 | 1/2019 | Venkatraman et al. | |
| 2019/0072912 A1 | 3/2019 | Pandya et al. | |
| 2019/0101870 A1 | 4/2019 | Pandya et al. | |
| 2019/0209031 A1 | 7/2019 | Ariyama et al. | |
| 2019/0220069 A1 | 7/2019 | Dusan | |
| 2020/0100684 A1 | 4/2020 | Lamego | |
| 2020/0229761 A1 | 7/2020 | Pandya et al. | |
| 2020/0233381 A1* | 7/2020 | Yang | H05K 1/115 |
| 2020/0356146 A1 | 11/2020 | Dusan | |
| 2021/0014617 A1 | 1/2021 | Dusan | |
| 2021/0204876 A1 | 7/2021 | Pandya et al. | |

FOREIGN PATENT DOCUMENTS

| | | |
|---|---|---|
| CN | 102246125 | 11/2011 |
| CN | 102483608 | 5/2012 |
| CN | 102867190 | 1/2013 |
| CN | 203732900 | 7/2014 |
| CN | 104050444 | 9/2014 |
| CN | 204515353 | 7/2015 |
| CN | 105339871 | 2/2016 |
| CN | 205041396 | 2/2016 |
| CN | 205121417 | 3/2016 |
| CN | 105556433 | 5/2016 |
| CN | 105955519 | 9/2016 |
| CN | 106236051 | 12/2016 |
| CN | 106388809 | 2/2017 |
| CN | 106462665 | 2/2017 |
| CN | 206209589 | 5/2017 |
| CN | 206324777 | 7/2017 |
| JP | 2001145607 | 5/2001 |
| JP | 2009519737 | 5/2009 |
| JP | 2016148657 | 8/2016 |
| KR | 20110012784 | 2/2011 |
| KR | 1020160041553 | 4/2016 |
| KR | 1020160145284 | 12/2016 |
| TW | 201610621 | 3/2016 |

(56) References Cited

FOREIGN PATENT DOCUMENTS

| TW | 201621491 | 6/2016 |
|---|---|---|
| TW | 201632136 | 9/2016 |
| WO | WO 15/030712 | 3/2015 |
| WO | WO 16/036747 | 3/2016 |
| WO | WO 16/040392 | 3/2016 |
| WO | WO 16/204443 | 12/2016 |

OTHER PUBLICATIONS

Ohgi et al., "Stroke phase discrimination in breaststroke swimming using a tri-axial acceleration sensor device," *Sports Engineering*, vol. 6, No. 2, Jun. 1, 2003, pp. 113-123.

Zijlstra et al., "Assessment of spatio-temporal gait parameters from trunk accelerations during human walking," *Gait & Posture*, vol. 18, No. 2, Oct. 1, 2003, pp. 1-10.

Onizuka et al., Head Ballistocardiogram Based on Wireless Multi-Location Sensors, 2015 EEE, pp. 1275-1278.

International Search Report and Written Opinion dated Mar. 27, 2019, PCT/US2018/048961, 18 pages.

Dozza et al., "A Portable Audio-biofeedback System to Improve Postural Control," Proceedings of the 26th Annual International Conference of the IEEE EMBS, San Francisco, CA, Sep. 1-5, 2004, pp. 4799-4802.

U.S. Appl. No. 16/118,282, filed Aug. 30, 2018, Clavelle et al.

U.S. Appl. No. 16/193,836, filed Nov. 16, 2018, Pandya et al.

Chen et al., "Dynamics Analysis and Simulation of the Wearable Power Assistance Robot," Experiment Science and Technology, 2009, 5 pages.

Nirjon et al., MusicalHeart: A Hearty Way of Listening to Music, SenSys 2012, Nov. 6-9, 2012, Toronto, Ontario, Canada, pp. 1-14.

\* cited by examiner

OPTICAL SENSOR SUBSYSTEM ADJACENT A COVER OF AN ELECTRONIC DEVICE HOUSING

CROSS-REFERENCE TO RELATED APPLICATION

This application claims the benefit under 35 U.S.C. § 119(e) of U.S. Provisional Patent Application No. 62/563,529, filed on Sep. 26, 2017, and entitled "Optical Sensor Subsystem Adjacent a Crystal Surface of an Electronic Device Housing," the contents of which are incorporated herein by reference as if fully disclosed herein.

FIELD

The described embodiments relate generally to a watch or other electronic device (e.g., another type of wearable electronic device). More particularly, the described embodiments relate to techniques for mounting an optical sensor subsystem adjacent a cover of a watch or other electronic device housing.

BACKGROUND

A watch or other electronic device may include a set of sensors for determining a set of biological parameters of a user that wears the device. The set of sensors may include an optical sensor, which optical sensor may include a light emitter and a light receiver. The light emitter may emit light toward the user (e.g., toward the skin of the user). A portion of the light may be absorbed by the user, and another portion of the light may be reflected from the user (e.g., reflected from an interior or exterior layer of the user's skin). The reflected portion of the light may be received by the light receiver. Circuitry associated with the light receiver may generate electrical signals (or values) corresponding to an amount, frequency, and/or intensity of the reflected light, or may generate electrical signals (or values) corresponding to changes in the amount or intensity of the reflected light over time. The amount, intensity, or changes in the reflected light may be correlated to, or used to derive, various biological parameters of the user, such as a heart rate of the user.

The optical sensor may be protected from contaminants (e.g., dust or moisture) by a transparent or translucent surface that forms part of the housing for the device. The manner in which the components of the device are manufactured or assembled can affect the degree to which the optical sensor is protected from contaminants, the performance of the optical sensor, the amount of power required to operate the optical sensor, the size or thickness of the device, and so on.

SUMMARY

Embodiments of the systems, devices, methods, and apparatus described in the present disclosure are directed to a watch or other electronic device (e.g., another type of wearable electronic device) that may be used to determine a set of biological parameters of a user that wears the device. The biological parameters may include, for example, a heart rate of a user that wears the device.

In a first aspect, the present disclosure describes a watch, comprising: a housing; a cover attached to the housing; a substrate; a set of light emitters adjacent a central portion of the cover and configured to emit light through the cover; a set of light receivers substantially surrounding the set of light emitters and positioned to receive a reflected portion of the light through the cover; and a set of light-blocking walls attaching the substrate to the cover; a lens attached to the cover and positioned between the set of light emitters and the cover; a light filter attached to the surface of the cover and positioned between at least one of the light receivers and the cover; a magnet attached to the substrate; and a processor configured to determine a biological parameter using the reflected portion of the light.

In another aspect, the present disclosure describes an electronic device, comprising: a housing; a cover attached to the housing and defining: a first surface interior to the electronic device; and a second surface exterior to the electronic device; an optical sensor subsystem attached to the first surface of the cover and comprising: a substrate; a light emitter attached to the substrate; a light receiver attached to the substrate and configured to receive light emitted by the light emitter and reflected from a medium adjacent the second surface of the cover; and a processor operationally connected to the light receiver and configured to determine a heart rate from the light received by the light receiver.

In still another aspect of the disclosure, a wearable electronic device is described. The wearable electronic device includes a housing, first and second electrodes, a lens, and a light filter. The housing includes a cover having a first surface interior to the electronic device and a second surface exterior to the electronic device. The first and second electrodes are on the second surface of the cover. An ink mask is also on the cover. The ink mask defines a first aperture and a second aperture between the first electrode and the second electrode. The lens is on the first surface of the cover and aligned with the first aperture, and the light filter is on the first surface of the cover and aligned with the second aperture.

In addition to the aspects and embodiments described above, further aspects and embodiments will become apparent by reference to the drawings and by study of the following description.

BRIEF DESCRIPTION OF THE DRAWINGS

The disclosure will be readily understood by the following detailed description in conjunction with the accompanying drawings, wherein like reference numerals designate like structural elements, and in which.

Figure 1:
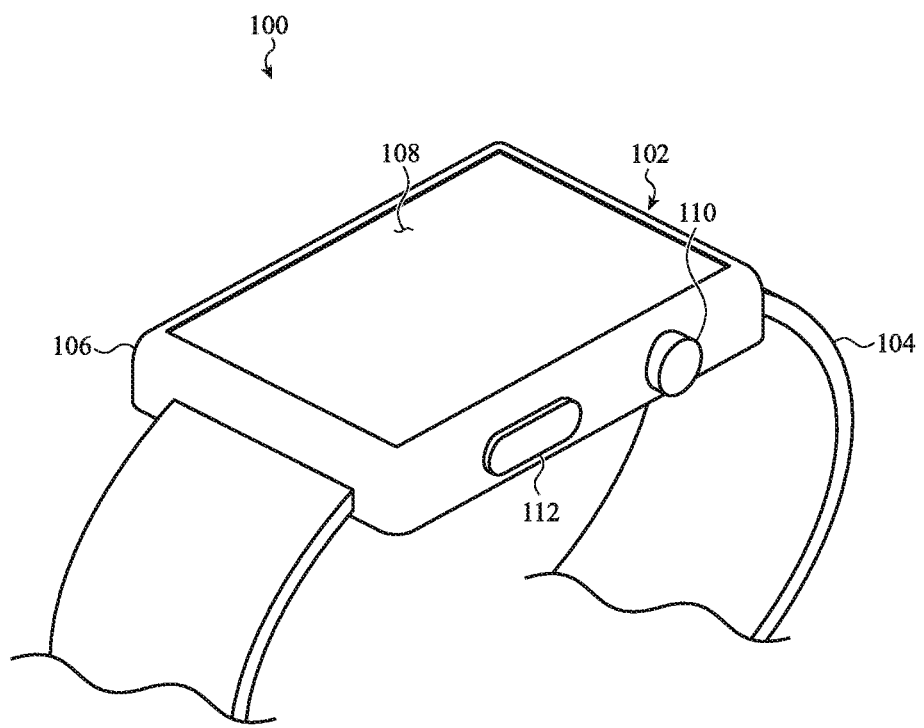
FIG. 1 shows an example of a watch that may incorporate an optical sensor subsystem adjacent a cover.

The use of cross-hatching or shading in the accompanying figures is generally provided to clarify the boundaries between adjacent elements and also to facilitate legibility of the figures. Accordingly, neither the presence nor the absence of cross-hatching or shading conveys or indicates any preference or requirement for particular materials, material properties, element proportions, element dimensions, commonalities of similarly illustrated elements, or any other characteristic, attribute, or property for any element illustrated in the accompanying figures.

Additionally, it should be understood that the proportions and dimensions (either relative or absolute) of the various features and elements (and collections and groupings thereof) and the boundaries, separations, and positional relationships presented therebetween, are provided in the accompanying figures merely to facilitate an understanding of the various embodiments described herein and, accordingly, may not necessarily be presented or illustrated to scale, and are not intended to indicate any preference or requirement for an illustrated embodiment to the exclusion of embodiments described with reference thereto.

DETAILED DESCRIPTION

Reference will now be made in detail to representative embodiments illustrated in the accompanying drawings. It should be understood that the following description is not intended to limit the embodiments to one preferred embodiment. To the contrary, it is intended to cover alternatives, modifications, and equivalents as can be included within the spirit and scope of the described embodiments as defined by the appended claims.

The following disclosure relates to techniques for mounting an optical sensor subsystem adjacent (e.g., directly on or abutting) a cover of a watch body or other electronic device housing. The optical sensor subsystem may function as, for example, an optical heart rate detector. An optical sensor or sensors of the optical sensor subsystem may be used to emit and receive light through the cover, and to measure, for example, properties of light reflected from a user of a device or other surface. Such measurements may be used by a processor of the electronic device to determine a biological parameter of a person, such as a person wearing or holding the electronic device. Sample properties that can be measured include amounts, intensities, or patterns of light. As one non-limiting example, the optical sensor subsystem may measure an amount of light reflected from the skin of the user; as the heart beats, blood is pumped into the skin. When blood pumps, the skin distends slightly and so more light is reflected from the skin than when the heart expands. Thus, as the optical sensor subsystem shines light onto the user's skin and receives reflected light, the amount of reflected light increases when the heart contracts and decreases when the heart increases. Thus, changes in a detected amount of reflected light may be directly correlated to, or otherwise used to determine, a heart rate (e.g., pulse). Further, insofar as the amplitude of reflected light is proportional to blood pressure of the pulse, such data may be used to determine blood pressure.

Measurements provided by the optical sensor subsystem may be converted to electrical signals or values (e.g., digital or analog values), for example. A processor may determine, from the measurements, signals, or values, a set of biological parameters of the user for which the measurements were obtained. The biological parameter(s) may include, for example, a heart rate, blood pressure, blood oxygenation, glucose level, and so on. Generally, the processor is operationally connected to the optical sensor, or at least to the light receiver.

In some embodiments, an optical sensor subsystem (such as an optical heart rate detector) may be attached directly on an interior surface of a cover, with a light-blocking wall abutting the cover between a light emitter and a light receiver of the optical sensor subsystem. The light-blocking wall may block a portion of light, emitted by the light emitter, which would otherwise impinge on the light receiver before passing through the cover. In some examples, the optical sensor subsystem may be at least partly attached to the cover via the light-blocking wall. In some embodiments, one or more discrete optical sensor subsystems may be attached to the surface of the cover. In some embodiments, the light-blocking wall may form a closed wall or boundary around the light emitter (or around a set of multiple light emitters) and block light emitted by the light emitter(s) from impinging on the light receiver(s) before passing through the cover. In other embodiments, the light-blocking wall may form a closed wall or boundary around the light receiver (or around a set of multiple light receivers) and block light emitted by the light emitter(s) from impinging on the light receiver(s) before passing through the cover.

The term "attached," as used herein, refers to two elements, structures, objects, parts or the like that are physically affixed to one another. The term "coupled," as used herein, refers to two elements, structures, objects, parts or the like that are physically attached to one another, operate with one another, communicate with one another, are in electrical connection with one another, or otherwise interact with one another. Accordingly, while two elements attached to one another are coupled to one another, the reverse is not required.

In the same or alternative embodiments, a light filter may be attached to the interior surface of the cover. The light filter may include one or more of a light control film, a light polarizer, an anti-reflective film, a reflective film, or a light absorber. The light filter may absorb, block, reflect, or otherwise limit the light receiver's receipt of a portion of light, emitted by the light emitter, which is reflected toward the light receiver at a high angle, which is typically greater than 45 degrees as measured with respect to a line perpendicular to the interior surface of the cover (and plane of the light filter). High angle light typically includes light that reflects from a surface other than an intended sample surface (e.g., from skin adjacent the exterior surface of the cover). The portion of light that is absorbed, blocked, or reflected by the light filter may include, for example, light emitted by the light emitter that reflects from the exterior surface of the cover or imperfections within the cover. In some embodiments, the light filter may be attached to the optical sensor subsystem, instead of to the interior surface of the cover, and may abut the cover or be positioned near but not on the cover when the optical sensor subsystem is attached to or otherwise positioned adjacent the interior surface of the cover. (In some embodiments the light filter may be considered part of the optical sensor subsystem.) The light passing through the filter may be received and properties of the light may be used by a processor to determine the biological parameter. Sample properties include light intensity, frequency, amplitude, an amount of received light, and so on.

Also in the same or alternative embodiments, a dark mask or ink mask (which ink mask may be a dark mask) may be applied to the interior or exterior surface of the cover. In some examples, the mask(s) may define apertures to limit what light emitted by the light emitter can propagate either out or in through the cover. In some examples, part or all of the mask(s) may allow certain wavelengths of light to pass, such as infrared wavelengths, while absorbing, blocking, or reflecting other wavelengths of light, such as visible wavelengths. In some examples, a mask may appear dark or opaque, but allow particular wavelengths of light to pass. In some examples, part or all of the mask(s) may absorb, block, or reflect all wavelengths of light. In some examples, part or all of the mask may prevent a user of the device from viewing components interior to the device.

Still further in the same or alternative embodiments, circuitry, a processing subsystem (such as a processor and/or associated substrate), a magnet (e.g., for inductive charging of the device), or other components may be attached to the optical sensor subsystem, and thereby to the interior surface of the cover. This processing subsystem may use properties of the light passing through the mask and/or filter to determine the biological parameter. For example, amounts, intensities, amplitudes, and/or wavelengths of light passing through the mask and/or filter, and received by the light receiver, may be used to determine a user's heart rate. Changes in such properties may correspond to, or otherwise indicate, changes in quantities blood flowing through a user's veins or arteries, and thus a user's heart rate.

The techniques and embodiments described herein can in some cases improve the degree to which the components of an optical sensor subsystem (e.g., a light emitter and a light receiver) are protected from contaminants. The techniques can also or alternatively improve the performance of the optical sensor, for example by enabling the optical sensor to be positioned closer to the cover, by enabling the optical sensor to be better aligned with the cover, or by limiting the impingement of unwanted light on the light receiver. Techniques and embodiments described herein also may reduce the amount of power required to effectively operate the optical sensor and thus optically determine a wearer's heart rate, for example by enabling the light emitter to be positioned closer to the light receiver while limiting the impingement of unwanted light on the light receiver. The techniques and/or embodiments can also or alternatively decrease the size or thickness of the device, for example by enabling a reduction in layer count or component count in the optical sensor subsystem, by enabling the optical sensor to be positioned closer to (such as directly on) the interior surface of the cover, or by enabling the optical sensor subsystem and in some cases other components to be attached to the interior surface of the cover.

These and other embodiments are discussed below with reference to FIGS. 1-16. However, those skilled in the art will readily appreciate that the detailed description given herein with respect to these figures is for explanatory purposes only and should not be construed as limiting.

Turning now to FIG. 1, an example of an electronic watch 100 that incorporates an optical sensor subsystem (which may function as an optical heart rate detector) adjacent a cover is shown. The watch may include a watch body 102 and a watch band 104. Other devices that may incorporate an optical sensor subsystem adjacent a cover include other wearable electronic devices, other timekeeping devices, other health monitoring or fitness devices, other portable computing devices, mobile phones (including smart phones), tablet computing devices, digital media devices, personal digital assistants, or the like.

The watch body 102 may include a housing 106. The housing 106 may include a front side housing member that faces away from a user's skin when the watch 100 is worn by a user, and a backside housing member that faces toward the user's skin when worn. Alternatively, the housing 106 may include a singular housing member, or more than two housing members. The one or more housing members may be metallic, plastic, ceramic, crystal, or other types of housing members (or combinations of such materials).

A cover 108 may be attached to a front side of the watch body 102 (i.e., facing away from a user's skin) and may protect a display at least partially within the housing 106. The display may be viewable by a user through the cover 108. In some cases, the cover 108 may be part of a display stack, which display stack may include a touch sensing or force sensing capability. The display may be configured to depict a graphical output of the watch 100, and a user may interact with the graphical output (e.g., using a finger or stylus). As one example, the user may select (or otherwise interact with) a graphic, icon, or the like presented on the display by touching or pressing on the display at the location of the graphic. The cover 108 may form a part of or be attached to the housing 106. In some examples, the cover 108 may be crystal, such as a sapphire crystal. The cover 108 may alternatively be formed of glass, plastic, or other materials. The cover 108 may be transparent or translucent to some or all wavelengths of electromagnetic radiation or light, which terms are used synonymously in this description.

The watch body 102 may include at least one input device or selection device, such as a crown, scroll wheel, knob, dial, button, or the like, which input device may be operated by a user of the watch 100. For example, the housing 106 may include an aperture through which a shaft of a crown 110 extends. The crown 110 may also include a crown body attached to the shaft, and may be accessible by a user exterior to the housing 106. The crown 110 may be manipulated by a user to rotate or translate the shaft (e.g., to provide an input to the watch 100). The shaft may be mechanically, electrically, magnetically, and/or optically coupled to components within the housing 106, for example. A user input through the crown 110 may be used, in turn, to manipulate or select various graphics displayed on the display, to adjust a volume of a speaker, to turn the watch 100 on or off, and so on. As another example, a user may use the crown 110 to initiate optical detection of a biological parameter such as a heart rate or blood pressure. In response to an input on or through the crown 110, a display of the electronic watch 100 may show a graphic representing the user's heart rate, blood pressure, or other biological parameter.

The housing 106 may also include an aperture through which a button 112 protrudes. The button 112 may likewise be used to provide input to the electronic device 100.

The housing 106 may include structures for attaching the watch band 104 to the watch body 102. In some cases, the structures may include elongate recesses or apertures through which ends of the watch band 104 may be inserted and attached to the watch body 102. In other cases (not shown), the structures may include indents (e.g., dimples or depressions) in the housing 106, which indents may receive ends of spring pins that are attached to or threaded through ends of a watch band to attach the watch band to the watch body.

The watch band 104 may be used to secure the watch 100 to a user, another device, a retaining mechanism, and so on.

In some examples, the watch 100 may lack the cover 108, the display, the crown 110, or the button 112. For example, the watch 100 may include an audio input or output interface, a touch input interface, a haptic (force) input or output interface, or other input or output interface that does not require the display, crown 110, or button 112. The watch 100 may also include the afore-mentioned input or output interfaces in addition to the display, crown 110, or button 112. When the watch 100 lacks the display, the front side of the watch 100 may be covered by a housing member that is opaque.

Figure 2:
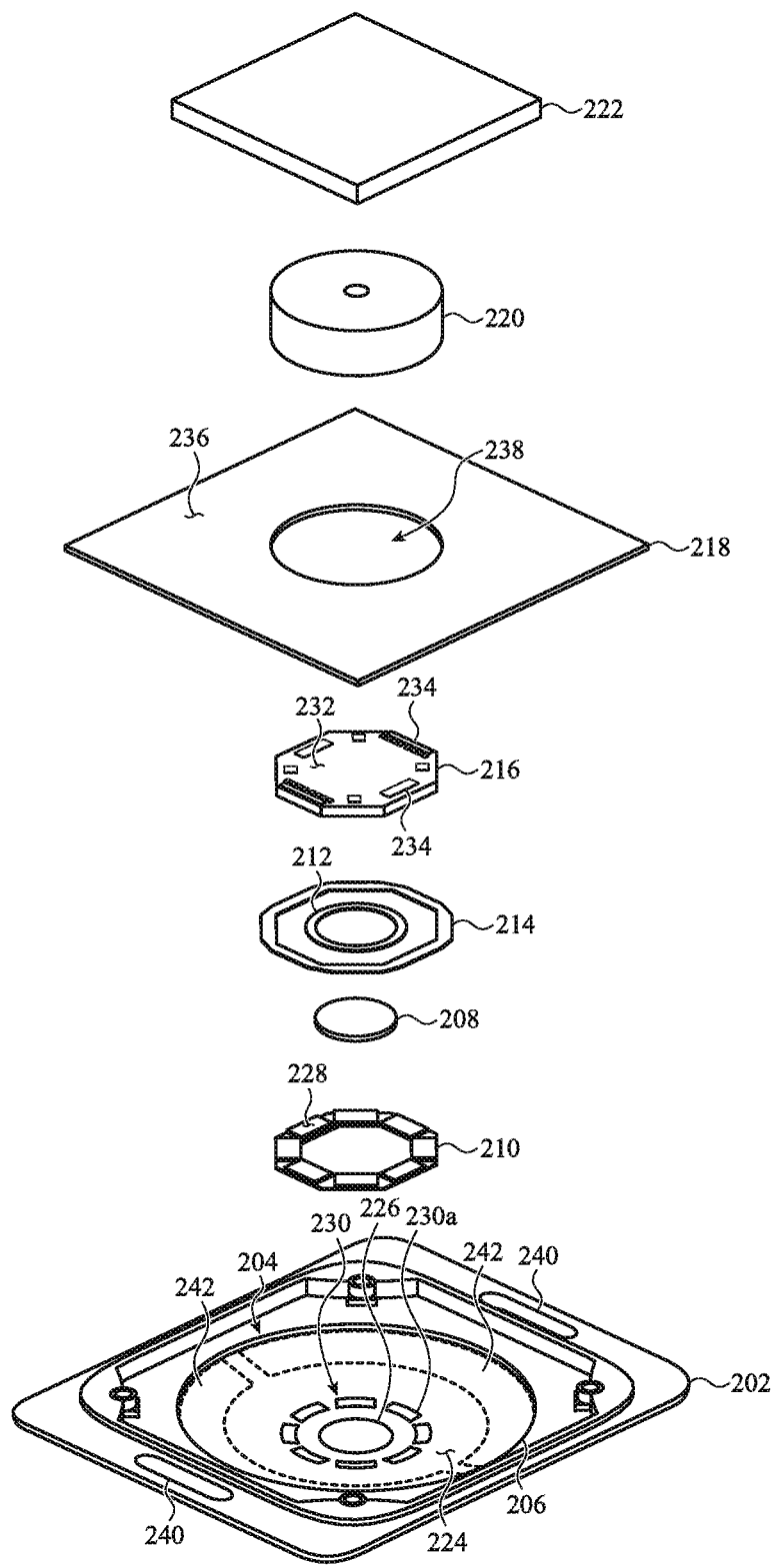
FIG. 2 shows an exploded view of components that may be attached to a cover attached to a backside housing member of a watch body.

FIG. 2 shows an exploded view of components that may be attached to a cover 204 attached to, and positioned within, a backside housing member of a watch body. In some examples, the components may be part of the watch body 102 shown in FIG. 1, and may be attached to, and positioned within, the housing 106 shown in FIG. 1. By way of example, FIG. 2 shows the components in relation to a backside housing member 202 (i.e., a skin-facing housing member) of a watch body such as the watch body 102. Also by way of example, the backside housing member 202 includes apertures 240 through which ends of a watch band may be inserted and attached to a watch body including the backside housing member 202.

A second cover 204 (e.g., a skin-facing cover) may be attached to the backside housing member 202 and form a part of (or be attached to) the housing of a watch body (e.g., a part of the watch body 102). The cover 204 may have a first surface that is interior to the watch body and a second surface that is exterior to the watch body. By way of example, the cover 204 has a round perimeter 206 and is fitted to a round aperture in the backside housing member 202. In other examples, the cover 204 may have a perimeter that is square, oval, or some other shape. Similarly, the aperture in the backside housing member 202 may be square, oval, or some other shape. The perimeter 206 of the cover 204 and the perimeter of the aperture need not have the same shape (e.g., the perimeter of the aperture in the backside housing member 202 may be smaller and differently shaped than the perimeter 206 of the cover 204). In some examples, the cover 204 may be a crystal, such as a sapphire crystal. The cover 204 may alternatively be formed of glass, plastic, or other materials. The cover 204 may be transparent or translucent to some or all wavelengths of electromagnetic radiation or light.

The exterior surface of the cover 204 may have a set of electrodes 242 thereon. The electrodes 242 may be positioned at the periphery of the cover 204 to enable optical communication in the region between the electrodes 242.

In some cases, the interior components shown in FIG. 2 may be attached to (and in some cases attached directly on) the first or interior surface of the cover 204. The components may include a lens 208, a light filter 210, one or more adhesives 212, 214, an optical sensor subsystem 216 (which includes one or more light emitters and one or more light receivers as discussed below with respect to FIG. 4), circuitry or a processing subsystem 218, a magnet 220, or a magnetic shield 222.

The lens 208 may abut, be attached to, or formed on the first or interior surface of the cover 204. By way of example, the lens 208 is aligned with the center of the cover 204. In some cases, the inner or exterior surface of the cover 204 may have a dark mask 224 (e.g., an ink mask) thereon. The dark mask 224 may define an aperture 226 (e.g., a first aperture or central aperture) that allows light of at least one wavelength to pass through the cover 204, and the lens 208 may be aligned with the aperture 226. In some cases, the lens 208 may be or include a Fresnel lens, a spherical lens, a diffuser film, or the like.

In some cases, the light filter 210 may include one or more segments 228, and each segment 228 may be attached to (e.g., laminated to) the interior surface of the cover 204 and positioned on the interior surface (e.g., adjacent or around the lens 208) to prevent a set of one or more light receivers on the optical sensor subsystem 216 from receiving a portion of the light that is emitted by a set of one or more light emitters on the optical sensor subsystem 216. The set of light emitters and set of light receivers are not shown in FIG. 2, and may be attached to an underside of the optical sensor subsystem 216. When the cover 204 includes the dark mask 224, the dark mask 224 may further define a second aperture 230a, or a set of apertures 230 including the second aperture 230a. The second aperture 230a or set of apertures 230 may be positioned adjacent or around the first aperture 226. In these embodiments, the segments 228 of the light filter 210 (or a light filter ring or other light filter configuration) may be aligned with (e.g., may cover) each of the apertures in the set of apertures 230.

As an example, FIG. 2 shows a dark mask 224 that defines a set of eight radial apertures 230 around a central aperture 226. Each segment 228 of the light filter 210 may block (e.g., absorb) a portion of light emitted by a set of light emitters that is part of the optical sensor subsystem 216, which portion of light reflects from a surface too close to (or within) the cover 204 (e.g., the exterior surface of the cover 204, imperfections within the cover 204, or a medium too close to the cover 204), such that the reflected light is not useful in a sensing operation for which the optical sensor subsystem 216 is designed. For example, when the optical sensor subsystem 216 and/or associated processor is configured to determine a biological parameter of a user, light reflected from the cover 204, or from the outer layer of skin of the user, may not have any relation to the biological parameter being determined and may not be useful. In some examples, the light filter 210 or segments 228 thereof may include at least one of a light control film, a light polarizer, an anti-reflective film, a reflective film, or a light absorber.

The optical sensor subsystem 216 may include a substrate 232 on which the set of one or more light emitters (e.g., LEDs) and the set of one or more light receivers (e.g., photodetectors, such as photodiodes) are attached. The light emitter(s) and light receiver(s) may be attached to or positioned on the substrate 232 to emit and receive light through the cover 204 and are part of the optical sensor subsystem 216. Generally, the optical sensor subsystem 216 includes light emitter(s) and light receiver(s) as discussed below with respect to FIG. 4, and may include the substrate 232. In some embodiments the optical sensor subsystem 216 may be defined to include one or more filters and/or masks, as discussed elsewhere herein. The optical sensor subsystem 216 may be attached to the cover 204 by one or more adhesives 212/214, such as pressure sensitive adhesives (PSAs) or heat-activated films (HAFs). In some cases, the set of light emitters may be centrally attached to the substrate 232, and a first wall may be attached to (e.g., formed on or bonded to) an underside of the substrate 232 surrounding the set of light emitters. The first wall may be attached to the interior surface of the cover 204 using a first ring of adhesive 212. The set of light receivers may be attached to the substrate 232 around the set of light emitters, between the first wall and a second wall attached to (e.g., formed on or bonded to) the underside of the substrate 232. The second wall may be attached to the interior surface of the cover 204 using a second ring of adhesive 214.

The substrate 232 of the optical sensor subsystem 216 may include various contacts, pads, traces, or other conductive structures 234 that enable the processing subsystem 218 to be electrically coupled to the set of light emitters and set of light receivers of the optical sensor subsystem 216. In some embodiments, the processing subsystem 218 includes a processor as described herein, which may be mounted to a substrate 236. The processing subsystem 218 may include substrate 236 (e.g., a printed circuit board (PCB)) that is attached to the optical sensor subsystem 216 and/or the processor, and thereby to the cover 204, via the conductive structures 234 and/or additional adhesive between the substrates 232, 236 of the optical sensor subsystem 216 and the processing subsystem 218. The substrates 232, 236 may also or alternatively be connected using mechanical fasteners (e.g., screws). The processing subsystem 218, and in particular its processor, may activate the light emitters and light receivers to perform a sensor function and may use data from the light receivers (and/or emitters) to determine a biological function such as a heart rate and/or blood pressure. As an example, light may be emitted from the light emitter, pass through the cover 204, be reflected from the user's skin and/or skin subsurface (potentially including veins, arteries, and/or capillaries), pass back through the cover 204 and a light filter (and, optionally, a mask defined in or on the cover) to be received by the light receiver. The processing subsystem 218 may use properties of the received light, such as an amount and/or amplitude of received light, to determine a user's heart rate, blood pressure, and so on. In some cases, the processing subsystem 218 may be attached to another structure within the watch body, and may be electrically connected to the conductive structures 234 of the optical sensor subsystem 216 by a flex circuit or other conductors.

In some embodiments, the substrate 236 of the processing subsystem 218 may have a hole 238 therein, and the magnet 220 may be aligned with the hole 238 and abut (or attached to) a surface of the substrate 232 opposite the cover 204. In some cases, the magnet 220 may be adhesively bonded to the substrate 232 of the optical sensor subsystem 216. The magnet 220 may inductively couple to a battery charger used for charging a battery included within the watch body, which battery may power components of the watch including the components of the optical sensor subsystem 216 and the processing subsystem 218.

The magnetic shield 222 may abut (or be attached to) the magnet 220. In some cases, the magnetic shield 222 may be adhesively bonded to the magnet 220. The magnetic shield may direct magnetic flux associated with the magnet 220 toward and out the cover 204 to improve inductive battery charging performance for a battery included within the watch body.

Direct or indirect mounting of the components shown in FIG. 2 to the interior surface of the cover 204 can reduce the height of the components when stacked.

Figure 3:
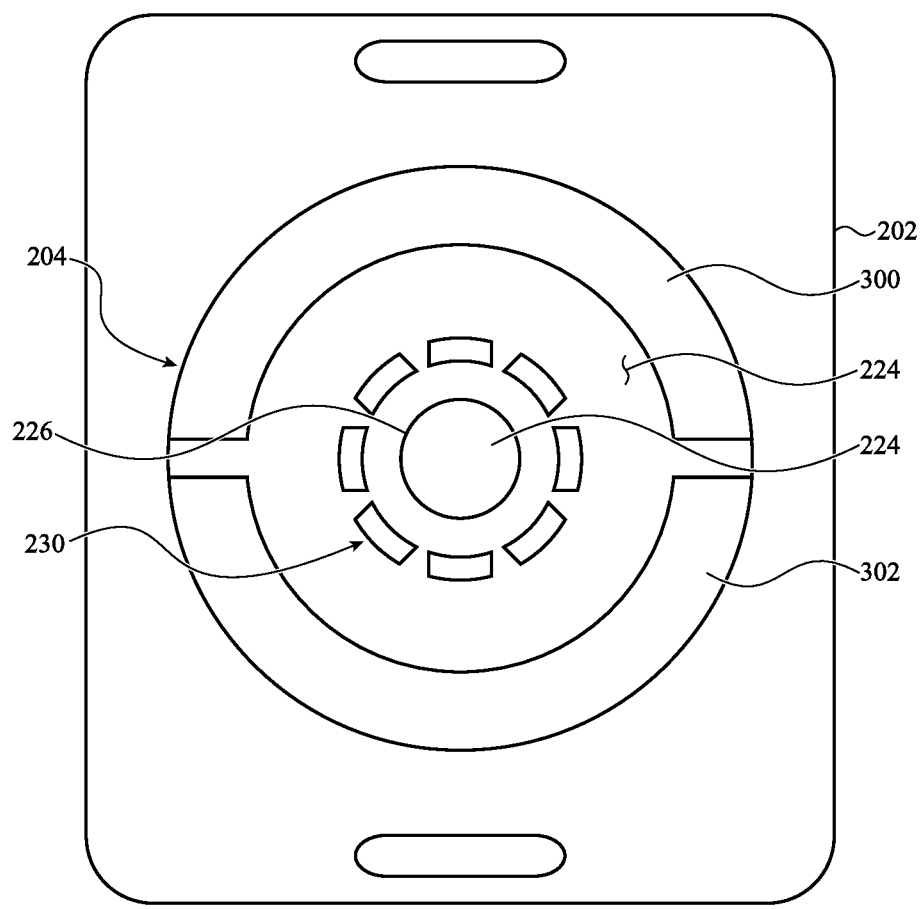
FIG. 3 shows the exterior surfaces (e.g., the skin-facing surfaces) of the backside housing member and cover shown in FIG. 2.

FIG. 3 shows the exterior surfaces (e.g., the skin-facing surfaces) of the backside housing member 202 and cover 204 (e.g., a crystal, glass, or plastic cover) shown in FIG. 2.

The exterior surface of the cover 204 may have a first electrode 300 and a second electrode 302 formed thereon. In some cases, the first and second electrodes 300, 302 may be semi-circle-shaped, and may be positioned around the central aperture 226 and set of apertures 230 formed in the dark mask 224. The first and second electrodes 300, 302 may extend to the edge of the cover 204, and in some cases may wrap around the perimeter of the cover 204 to the interior surface of the cover 204, or be connected to conductive vias formed in the cover 204, or otherwise electrically connect to elements within a watch body that apply a signal to, or receive a signal sensed by, one or both of the first and second electrodes 300, 302. In some cases, the first and second electrodes 300, 302 may be electrically insulated from the backside housing member 202 (e.g., by a non-conductive gasket or adhesive), or the backside housing member 202 may be non-conductive. In some cases, the first and second electrodes 300, 302 may include a metallic material. The first and second electrodes 300, 302 may be configured to provide and/or measure data used by the processing subsystem 218 (and in particular a processor thereof) to determine a second biological parameter, such as an electrocardiogram.

Figure 4:
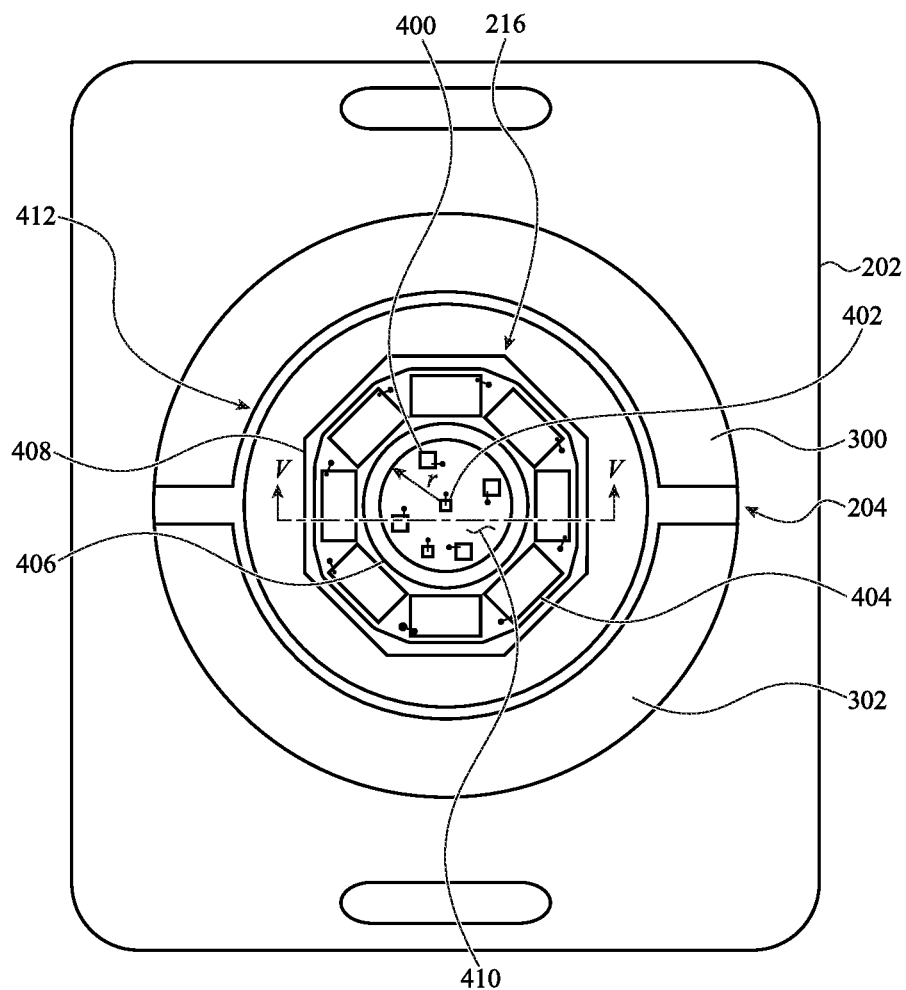
FIG. 4 shows another view of the exterior surfaces of the backside housing member and cover shown in FIG. 2, with a central portion of the dark mask removed to show components of the optical sensor subsystem adjacent the cover.

FIG. 4 shows another view of the exterior surfaces of the backside housing member 202 and cover 204 (e.g., a crystal, glass, or plastic cover) shown in FIG. 2. However, in contrast to the view shown in FIG. 3, a central portion of the dark mask 224, in addition to the lens 208, has been removed to show components of the optical sensor subsystem 216 adjacent the cover 204.

As shown in FIG. 4 the optical sensor subsystem 216 may include one or more light emitters 400, 402 (e.g., LEDs), one or more light receivers 404 (e.g., photodetectors), a set of one or more walls 406, 408, and a substrate 410. The light emitter(s) 400, 402, light receiver(s) 404, and set of one or more walls 406, 408 may be attached to the substrate 410, and the substrate 410 (with light emitter(s) 400, 402, light receiver(s) 404, and walls 406, 408 thereon) may be attached to the interior surface of the cover 204 by the set of one or more walls 406, 408. By way of example, the set of one or more walls may include a closed form inner wall 406 having a circular shape, and a closed form outer wall 408 having an octagonal shape. In other examples, one or both of the walls 406, 408 may have one or more openings therein, or may be replaced by a plurality of discrete walls, or have a shape other than the shape shown. In some cases, the set of one or more walls 406, 408 may only include the inner wall 406, or may include more than two walls. The inner wall 406, and in some cases the outer wall 408, may be light-blocking walls. Light-blocking walls can help to limit the light received by the light receiver(s) 404 to light that is reflected from a medium (e.g., skin) adjacent the exterior surface of the cover 204.

By way of example, the set of one or more light emitters 400, 402 may include a first set of one or more light emitters 400 configured to emit light having a first wavelength (e.g., a set of visible light emitters, such as a set of four green light emitters) and a second set of one or more light emitters 402 configured to emit light having a second wavelength that differs from the first wavelength (e.g., a set of two infrared (IR) light emitters). Alternatively, the set of light emitters may include light emitters configured to emit the same wavelength of light, or one or more light emitters that are tunable to emit different wavelengths of light. The light emitters 400, 402 may be attached to the substrate 410, and the optical sensor subsystem 216 may be attached to the cover 204, such that the set of one or more light emitters 400, 402 is positioned below the interior surface of the cover 204.

In some cases light emitters that emit different wavelengths may be activated at different times or for different purposes. For example, IR light emitters may be operated at a lower power and may be used for background heart rate detection, blood pressure detection, and/or watch "off-wrist" detection.

Also by way of example, the set of one or more light receivers 404 includes eight rectangular photodetectors. In other examples, the optical sensor subsystem 216 may include more or fewer light receivers 404, and/or light receivers having different shapes. In some cases, the light receivers 404 may be defined along the perimeter of a ring of photosensitive material.

The light emitters 400, 402 may be operated individually, or may be grouped and operated within two or more channels of operation. Similarly, the light receivers 404 may be operated individually, or may be grouped and operated within two or more channels of operation.

In some cases, the one or more light emitters 400, 402 and one or more light receivers 404 of the optical sensor subsystem 216 may be positioned interior from a perimeter 412 defined by the first and second electrodes 300, 302 (i.e., between the electrodes 300, 302). In some cases, the mounting of the light emitter(s) 400, 402 (i.e., the set of light emitters) and light receiver(s) 404 (i.e., the set of light receivers) to the substrate 410, and the attachment of the substrate 410 to the interior surface of the cover 204, may position the light emitter(s) 400, 402 adjacent a central portion of the cover 204 and position the light receiver(s) 404 radially further from the central portion of the cover 204 than the light emitter(s) 400, 402 (i.e., the light receiver(s) 404 may be positioned adjacent a portion of the cover 204 that is radial outward from the central portion). The central portion may have a circular boundary defined by a radius, r. In other cases, the central portion may have a boundary of another shape. In some cases, the inner wall 406 may define the boundary of the central portion of the cover 204. When the light receiver(s) 404 include multiple light receivers, or when the light receiver(s) include one or more elongate arced or rectangular segments, the light receiver(s) 404 may substantially surround the light emitter(s) 400, 402. For example, discrete light receivers may be positioned at four or more locations around the light emitter(s) 400, 402, or one or more elongate arced or rectangular segments may occupy at least half of a circumference or perimeter surrounding the light emitter(s) 400, 402.

Figure 5:
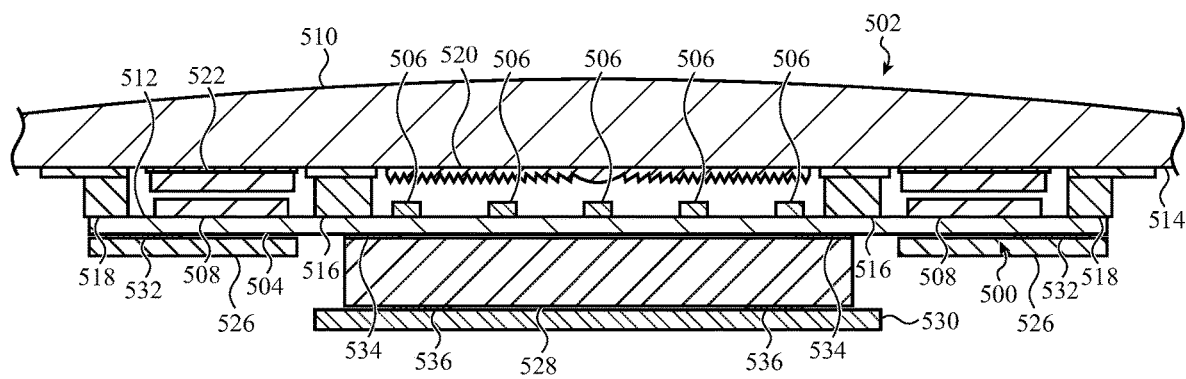
FIG. 5 shows a sample cross-section of an optical sensor subsystem adjacent a cover of a watch housing.

FIG. 5 shows a cross-section of an optical sensor subsystem 500 adjacent a cover 502 (e.g., a crystal, glass, or plastic cover) of a watch body housing (or other electronic device housing). In some examples, the cross-section may be a cross-section of the optical sensor subsystem 216 and cover 204 shown in FIGS. 2-4. The optical sensor subsystem 500 includes a substrate 504 on which a set of light emitters 506 (e.g., LEDs) and a set of light receivers 508 (e.g., photodetectors, such as photodiodes) are attached. The light emitters 506 may be attached to or positioned on the substrate 504 to project light through the cover 502, and the light receivers 508 may be attached to or positioned on the substrate 504 to receive light emitted by the light emitters 506 and reflected from a medium (e.g., a user's wrist) adjacent the exterior surface 510 of the cover 502. In some examples, and as shown, the light emitters 506 and light receivers 508 may be attached to a surface 512 of the substrate 504 facing an interior surface 514 of the cover 502. Alternatively, the light emitters 506 or light receivers 508 may be attached to a surface of the substrate 504 facing away from the cover 502, and the light emitters 506 or light receivers 508 may emit or receive light through apertures in the substrate 504.

Figure 6:
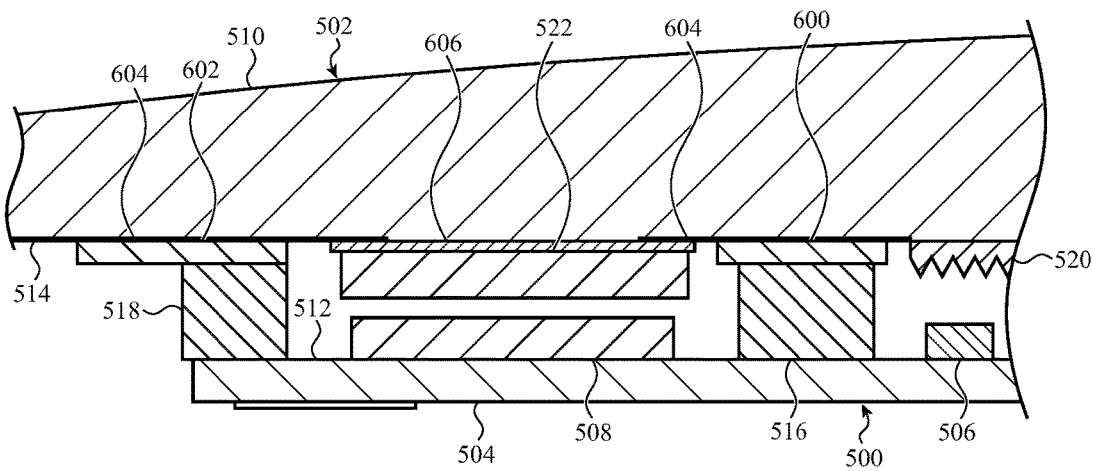
FIG. 6 shows an enlarged view of a portion of the apparatus shown in FIG. 5.

The optical sensor subsystem 500 may be attached (e.g., bonded) to the cover 502 by an adhesive 600, 602 such as a PSA or HAF, as shown in FIG. 6, which shows an enlarged view of a portion of the apparatus shown in FIG. 5. In some cases, the set of light emitters 506 may be centrally attached to the substrate 504, and a first wall 516 (e.g., a circular-shaped wall) may be attached to (e.g., be attached to or formed on) the substrate 504 surrounding the set of light emitters 506 (e.g., the first wall 516 may be positioned between the set of light emitters 506 and the set of light receivers). The first wall 516 may be positioned around the set of light emitters 506 and attached (e.g., bonded) to the interior surface 514 of the cover 502 using an adhesive (e.g., a first ring of adhesive 600; see FIG. 6). The set of light receivers 508 may be attached to the substrate 504 around the light emitters 506, between the first wall 516 and a second wall 518 (e.g., an octagonal-shaped wall) that is positioned around the set of light receivers 508 and attached to (e.g., be attached to or formed on) the substrate 504. The second wall 518 may also be attached (e.g., bonded) to the interior surface 514 of the cover 502 using an adhesive 602 (e.g., a second ring of adhesive). In some cases, the interior surface 514 of the cover 502, or at least the portion of the interior surface 514 over which the optical sensor subsystem 500 is attached, may be flat. In an alternative embodiment, the set of light receivers 508 could be attached to the substrate 504 within the first wall 516, and the set of light emitters 506 could be attached to the substrate 504 between the first and second walls 516, 518.

In some embodiments, the walls 516 and 518 may be made of high-temperature plastic. In some cases, the walls 516 and 518 may be injection molded as separate components and placed on (and bonded to) the substrate 504 before the optical sensor subsystem 500 is attached to the cover 502 via the walls 516, 518. In some examples, the walls 516, 518 may be bonded to the substrate 504 using a thermoset adhesive. In some embodiments, one or both of the walls 516 and 518 (and in particular, the outer wall 518) may be formed by layers of the substrate 504 (e.g., by additional FR4 layers of a printed circuit board). In some cases, one or both of the walls 516, 518 may be light-blocking walls. The outer wall 518 may be less light-blocking than the inner wall 516 (or non-light blocking), in some examples, because the outer wall 518 may not need to form an optical barrier between the light emitters 506 and the light receivers 508. When the walls 516 and 518 are made of different materials or are otherwise subject to small differences in height, an HAF or other flowable adhesive may be used to attach the walls 516, 518 to the interior surface 514 of the cover, because a flowable adhesive may better account for non-planar wall heights.

An optional lens 520 (e.g., a Fresnel lens, a spherical lens, a diffuser film, or the like) may be attached to the interior surface 514 of the cover 502, between the light emitters 506 and cover 502. An optional light filter 522 (e.g., a light control film, a light polarizer, an anti-reflective film, a reflective film, or a light absorber) may be attached to the interior surface 514 of the cover 502, between the light receivers 508 and cover 502. By mounting the optical sensor subsystem 500 directly on the cover 502 and sealing the light emitters 506 and light receivers 508 within cavities formed by the substrate 504, walls 516 and 518, and interior surface 514 of the cover 502, lower cost and/or lower height light emitters 506 and light receivers 508 (i.e., emitters and receivers without encapsulants applied directly thereto) can be used, potentially reducing the cost and height of the apparatus shown in FIG. 5. Also, by mounting the lens 520 and light filter 522 to the interior surface 514 of the cover 502, the lens 520 and light filter 522 may be attached to the cover 502 in one set of operations, and the walls 516, 518 of the optical sensor subsystem 500 may be aligned with the cover 502, the lens 520, and the light filter 522 and attached to the cover 502 in a separate operation, with the lens 520 and light filter 522 extending into cavities defined by the optical sensor subsystem 500 to reduce the height of the apparatus (e.g., compared to allocating a separate layer to optics components including the lens 520 and light filter 522).

In some embodiments, a processing subsystem 524 may be electrically or mechanically coupled to the bottom side of the optical sensor subsystem 500. The processing subsystem may be electrically coupled to the light emitters 506 and light receivers 508 of the optical sensor subsystem 500. The processing subsystem 524 may include a substrate 526 (e.g., a PCB) that is attached to the optical sensor subsystem 500, and thereby to the cover 502, via conductive or non-conductive structures 532, including metallic bonds, adhesive, or mechanical fasteners (e.g., screws). The processing subsystem 524 may activate the light emitters and light receivers to perform a sensor function (e.g., to optically determine a heart rate and/or blood pressure).

In some embodiments, the substrate 526 of the processing subsystem 524 may have a hole therein, and a magnet 528 may be aligned with the hole and abutted to (or attached to) the substrate 526. In some cases, the magnet 528 may be adhesively bonded to the substrate 504 of the optical sensor subsystem 500. The magnet 220 may be adhesively bonded to the substrate 504 using, for example, a PSA and/or liquid adhesive 534. In some cases, the magnet 220 may be bonded to the substrate 504 below the wall 516, to reduce the likelihood that the magnet 220 will cause the substrate 504 to bend (which may interfere with operation of the optical sensor components). The magnet 528 may be inductively couple to a battery charger used for charging a battery included within the watch body, which battery may power components of the watch including the components of the optical sensor subsystem 500 and the processing subsystem 524.

A magnetic shield 530 may abut (or be attached to) the magnet 528. In some cases, the magnetic shield 530 may be adhesively bonded to the magnet 528 using an adhesive 536. The magnetic shield 530 may direct magnetic flux associated with the magnet 528 toward the optical sensor subsystem 500 and out the cover 502, to improve inductive battery charging performance for a battery included within the watch body.

Referring in more detail to FIG. 6, a dark mask 604 may be applied to the interior surface 514 of the cover 502, between the lens 520 and the light filter 522. In some cases, the dark mask 604 may partially overlap the light filter 522 or light receiver 508. In some cases, an inner ring of the dark mask 604 may have a width (e.g., along a radius of the cover 502) that is greater than a width of the first wall 516, with the first wall 516 being positioned below the dark mask 604. In some cases, the width of the inner ring of the dark mask 604 may be approximately 0.8-1.0 millimeter (mm). The width of the inner ring of the dark mask 604 may be selected, prior to manufacture, to limit which rays of light emitted by the light emitter 506 are received by the light receiver 508 (e.g., only those rays that reflect from a medium (e.g., a user's skin) at a desired distance from the exterior surface 510 of the cover 502) and enter the cover 502 at a low angle with respect to perpendicular to the interior surface 514 of the cover 502. In some cases, the inner ring of the dark mask 604 may be considered part of the first wall 516 (e.g., a cap of the first wall 516). Alternatively, the first wall 516 may be considered to be a separate component positioned under the dark mask 604. In further examples, the first wall 516 may have a same width as the inner ring of the dark mask 604, or the inner ring of the dark mask 604 may not be positioned above the first wall 516 (or may not be applied to the cover 502 at all).

After the dark mask 604 is applied to the cover 502, or when the dark mask 604 is not applied to the cover 502, an adhesive 606 may be applied to the cover 502 for attaching the light filter 522 to the cover 502, or the light filter 522 may have an adhesive applied to one side thereof for attachment of the light filter 522 to the cover 502, or an adhesive may be applied to surfaces of the cover 502 and the light filter 522, or the light filter 522 may be formed directly on the cover 502 (but in some cases, partially over the dark mask 604).

Figure 7:
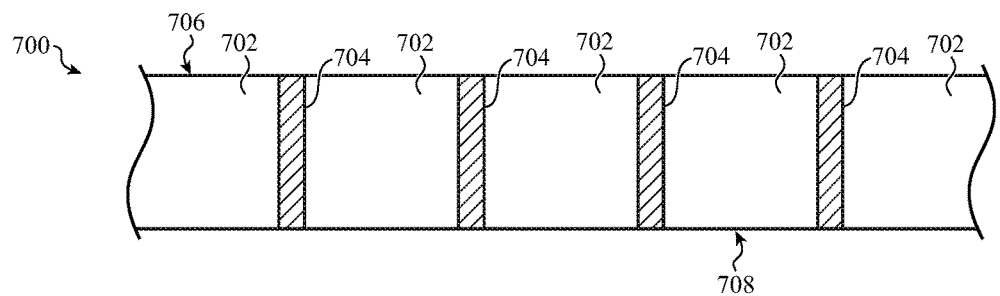
FIG. 7 shows an example of a light filter.

FIG. 7 shows an example of a light filter 700, such as an example of any of the light filters shown in FIGS. 2-6. As shown, the light filter 700 may include first portions 702 that are translucent to one or more wavelengths of light, and second portions 704 that are opaque to the one or more wavelengths of light. The translucent portions 702 and opaque portions 702 may be interleaved. In some examples, the opaque portions 704 may be oriented perpendicular to first and second opposing surfaces 706, 708 of the cover. In other examples, the opaque portions 704 may be oriented at an angle between 0 and 90 degrees with respect to the first and second opposing surfaces 706, 708 (and to the interior surface of a cover). In some cases, the translucent portions 702 may be wider than the opaque portions 704. In some examples, the opaque portions 704 may be oriented in lines that are tangent to a radius of a cover, or in concentric arcs with respect to an axis perpendicular to the interior surface of a cover. In some examples, the opaque portions 704 may absorb, block, not reflect, or reflect particular (or all) wavelengths of light.

Figure 8:
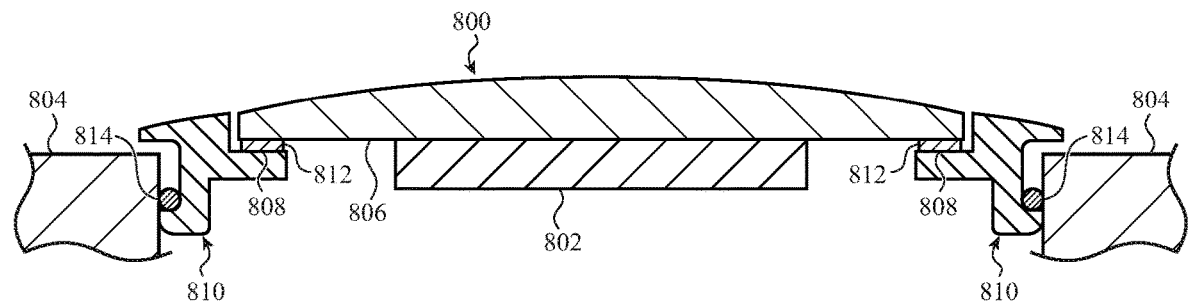
FIG. 8 shows an example cover, optical sensor subsystem, and housing member of an electronic device.

FIG. 8 shows an example cover 800 (e.g., a crystal, glass, or plastic cover), optical sensor subsystem 802, and housing member 804 of an electronic device. As shown, the interior surface 806 of the cover 800 may be attached to a shelf 808 of a carrier member 810 using an adhesive 812. A gasket 814 may be fitted around a perimeter of the carrier member 810 (e.g., in a recess around the perimeter of the carrier member 810). The carrier member 810 with attached cover 800 and gasket 814 may then be inserted into an aperture within the housing member 804. In other embodiments, a cover with attached optical sensor subsystem may be attached to a housing member of an electronic device in other ways, including before the optical sensor subsystem is attached to the cover, or using various types of adhesives, gaskets, and the like.

Figure 9:
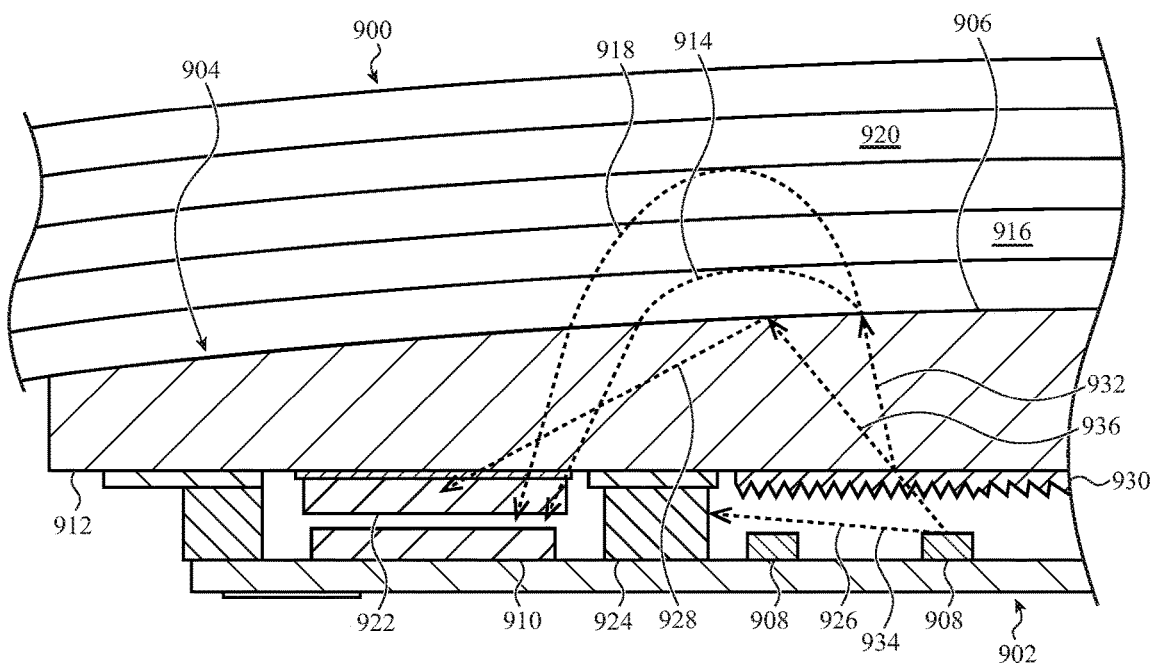
FIG. 9 shows an example portion of a watch body adjacent skin of a user.

FIG. 9 shows an example portion of a watch body adjacent skin 900 of a user (e.g., while a watch including the watch body is worn by the user). The portion of the watch body includes a portion of an optical sensor subsystem 902 adjacent a cover 904 (e.g., a crystal, glass, or plastic cover), as described for example with reference to FIGS. 2-6 and 8. The watch body may be oriented such that an exterior surface 906 of the cover 904 is adjacent skin 900 of the user's wrist.

A control system, included in the optical sensor subsystem 902 or otherwise connected to the optical sensor subsystem 902 and housed within the watch body, may simultaneously or sequentially activate a light emitter (or set of light emitters 908) and a light receiver 910 (or set of light receivers) to cause the light emitter(s) 908 to emit light and the light receiver 910 to receive light. The emitted light may pass through the interior surface 912 of the cover 904 and travel partially or wholly through the cover 904.

In some cases, a first portion of the light 932 emitted by a light emitter 908 may pass through the interior and exterior surfaces 912, 906 of the cover 904 and be reflected by a layer of the skin 900. As examples, FIG. 9 shows the first portion of light 932 as including a first ray of light 914 that reflects from a second layer 916 of the skin 900 and a second ray of light 918 that reflects from a fourth layer 920 of the skin 900. More than one ray of light may reflect from each of these (and other) layers of the skin 900. In some examples, the light emitter 908 may be configured to emit light that penetrates 0-2 millimeter (mm) of the skin 900. The light emitter 908 may be configured to emit light having a particular wavelength (e.g., frequency), intensity, or other preconfigured or programmable parameter. The rays of light 914, 918 of the first portion of light 932 may be reflected toward the light receiver 910 and pass through the cover 904 at a low enough angle with respect to perpendicular to the interior surface 912 of the cover 904 (and plane of a light filter 922) that the rays of light 914, 918 pass through the light filter 922 and are received by the light receiver 910.

A second portion of the light 934 emitted by a light emitter 908 may travel toward the cover 904 at a high angle (typically substantially greater than 45 degrees, as measured with respect to a line perpendicular to the interior surface 912 of the cover 904, such that the light may not penetrate the cover 904. To prevent the second portion of light 934 from reflecting off the interior surface 912 of the cover 904 and toward the light receiver 910, a light-blocking wall 924 may be positioned between the light emitter 908 and light receiver 910, abutting the interior surface 912 of the cover 904. The light-blocking wall 924 may prevent the light receiver 910 from receiving the second portion of light 934. In some cases, the second portion of light 934, including a ray of light 926, may be absorbed by the light-blocking wall 924. Because the second portion of light 934 is not reflected from the cover 904 or the skin 900, the second portion of light 934 may be referred to herein as non-reflected light.

A third portion of the light 936 emitted by a light emitter 908 may reflect from the exterior surface 906 of the cover 904, or from imperfections within the cover 904, or in some cases a layer of the skin 900 (e.g., an outer layer of the skin 900). By way of example, FIG. 9 shows the third portion of light 936 as including a ray of light 928 that reflects from the exterior surface 906 of the cover 904. Because the ray of light 928 is reflected from a location closer to the light receiver 910 and light filter 922, and because the ray of light 928 is reflected toward the light receiver 910 at a high angle (typically greater than 45 degrees, as measured with respect to a line perpendicular to the interior surface 912 of the cover 904 (and plane of the light filter 922)), the ray of light 928 is blocked from reaching the light receiver 910 by the light filter 922. In some cases, the ray of light 928 may be absorbed by the light filter 922.

A lens 930 may redirect the first and third portions of light 932, 936 as the portions of light travel from a light emitter 908 toward the skin 900 of the user. In some cases (e.g., when the lens 930 includes a Fresnel lens), the lens 930 may collimate the first and third portions of light 932, 936 (or redirect the first and third portions of light 932, 936 to move rays of the light closer to a collimated form).

Figure 10:
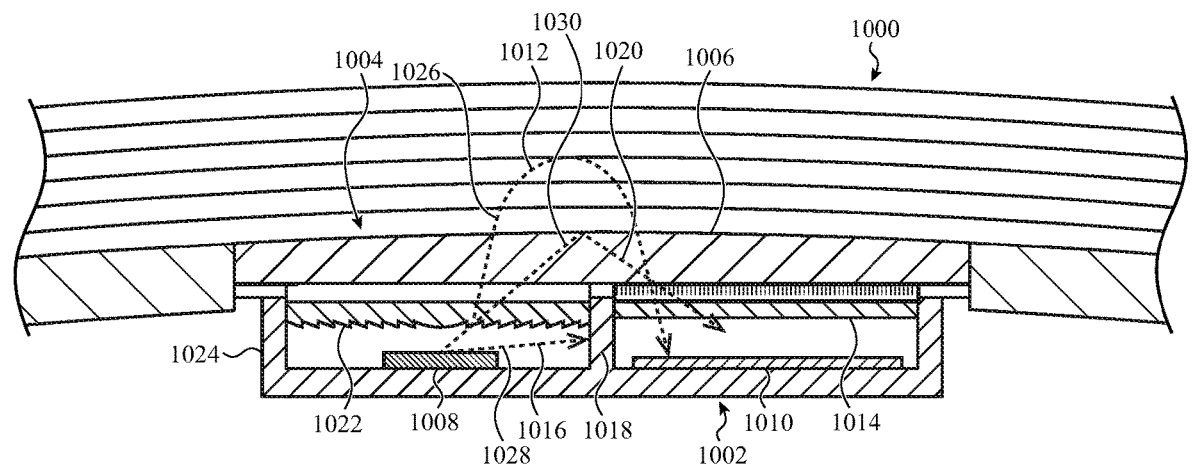
FIG. 10 shows another example portion of a watch body adjacent skin of a user.

FIG. 10 shows another example portion of a watch body adjacent skin 1000 of a user (e.g., while a watch including the watch body is worn by the user). The portion of the watch body includes a portion of an optical sensor subsystem 1002 adjacent a cover 1004 (e.g., a crystal, glass, or plastic cover), as described for example with reference to FIGS. 2-6 and 8. The watch body may be oriented such that an exterior surface 1006 of the cover 1004 is adjacent skin 1000 of the user's wrist.

A control system, included in the optical sensor subsystem 1002 or otherwise connected to the optical sensor subsystem 1002 and housed within the watch body, may simultaneously or sequentially activate a light emitter 1008 and a light receiver 1010 to cause the light emitter 1008 to emit light and the light receiver 1010 to receive light. The emitted light may pass through the interior surface of the cover 1004 and travel partially or wholly through the cover 1004.

Similarly to the example described with reference to FIG. 9, a first portion of the light 1026 emitted by the light emitter 1008, including a ray of light 1012, may pass through the interior and exterior surfaces of the cover 1004 and be reflected by a layer of the skin 1000. The first portion of light 1026 may be reflected toward the light receiver 1010 and pass through the cover 1004 at a low enough angle with respect to perpendicular to the interior surface of the cover 1004 (and plane of a light filter 1014) that the light passes through the light filter 1014 and is received by the light receiver 1010.

A second portion of the light 1028 emitted by the light emitter 1008, including a ray of light 1016, may travel toward the cover 1004 at a high angle (typically substantially greater than 45 degrees, as measured with respect to a line perpendicular to the interior surface of the cover 1004), such that the light may not penetrate the cover 1004. To prevent the second portion of light 1028 from reflecting off the interior surface of the cover 1004 and toward the light receiver 1010, a light-blocking wall 1018 may be positioned between the light emitter 1008 and light receiver 1010, abutting the interior surface of the cover 1004. The light-blocking wall 1018 may prevent the light receiver 1010 from receiving the second portion of light 1028. In some cases, the second portion of light 1028 may be absorbed by the light-blocking wall 1018. Because the second portion of light 1028 is not reflected from the cover 1004 or the skin 1000, the second portion of light 1028 may be referred to herein as non-reflected light.

A third portion of the light 1030 emitted by the light emitter 1008, including a ray of light 1020, may reflect from the exterior surface 1006 of the cover 1004, or from imperfections within the cover 1004, or in some cases a layer of the skin 1000 (e.g., an outer layer of the skin 1000). Because the third portion of light 1030 is reflected from a location closer to the light receiver 1010 and light filter 1014, and because the third portion of light 1030 is reflected toward the light receiver 1010 at a high angle (typically greater than 45 degrees, as measured with respect to a line perpendicular to the interior surface of the cover 1004 (and plane of the light filter 1014)), the third portion of light 1030 is blocked from reaching the light receiver 1010 by the light filter 1014. In some cases, the third portion of light 1030 may be absorbed by the light filter 1014.

A lens 1022 may redirect the first and third portions of light 1026, 1030 as the portions of light travel from the light emitter 1008 toward the skin 1000 of the user. In some cases (e.g., when the lens 1022 includes a Fresnel lens), the lens 1022 may collimate the first and third portions of light 1026, 1030 (or redirect the first and third portions of light 1026, 1030 to move rays of the light closer to a collimated form). In contrast to other optical sensor subsystem embodiments shown in the present disclosure, the embodiment shown in FIG. 10 shows the lens 1022 attached and/or positioned between walls 1018, 1024 of the optical sensor subsystem 1002 (instead of to the interior surface of the cover 1004). In this configuration, the lens 1022 may be separated from the interior surface of the cover 1004, as shown, or abutted to the interior surface of the cover 1004 (not shown).

Figure 11:
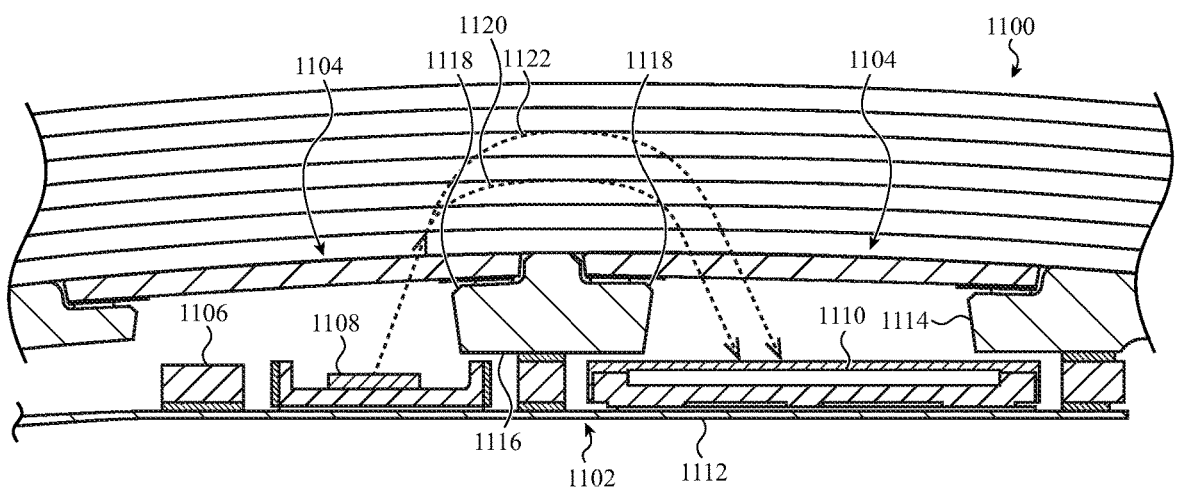
FIG. 11 shows still another example portion of a watch body adjacent skin of a user.

FIG. 11 shows another example portion of a watch body adjacent skin 1100 of a user (e.g., while a watch including the watch body is worn by the user). The portion of the watch body includes a portion of an optical sensor subsystem 1102 adjacent a split cover 1104 (i.e., a cover formed of two or more separate pieces, or a cover having an elongate slit therein). The watch body may be oriented such that an exterior surface of the split cover 1104 is adjacent skin 1100 of the user's wrist.

A control system 1106, included in the optical sensor subsystem 1102 or otherwise connected to the optical sensor subsystem 1102 and housed within the watch body, may simultaneously or sequentially activate a light emitter 1108 and a light receiver 1110 to cause the light emitter 1108 to emit light and the light receiver 1110 to receive light. The emitted light may pass through the interior surface of the split cover 1104 and travel partially or wholly through the split cover 1104.

Similarly to the examples described with reference to FIGS. 9 and 10, portions 1120, 1122 of the light emitted by the light emitter 1108 may pass through the interior and/or exterior surfaces of the split cover 1104, and reflections thereof may or may not be received at the light receiver 1110.

In contrast to other embodiments shown in the present disclosure, the optical sensor subsystem 1102 includes a substrate 1112 on which components such as the light emitter 1108 and light receiver 1110 are attached, and the substrate 1112 is attached to a housing member 1114 of the watch body instead of being attached to the interior surface of the split cover 1104. The split cover 1104 may also be attached to the housing member 1114.

Also in contrast to other embodiments shown in the present disclosure, the optical sensor subsystem 1102 is positioned adjacent a split cover 1104. The split cover 1104 enables a light-blocking wall 1116 to extend through the split in the split cover 1104, which wall 1116 may block more unwanted portions of light (e.g., portions of light that are not reflected by the skin 1100 of the user) from being received at the light receiver 1110. However, the light-blocking wall 1116 may need to be wider than other light-blocking walls described herein, to provide a surface 1118 that may be sealed to the interior surface of the split cover 1104. The greater width of the light-blocking wall 1116 may increase the distance that light emitted by the light emitter 1108 travels to reach the light receiver 1110, and may in some cases necessitate operating the light emitter 1108 at a higher transmit power (e.g., higher intensity). The seal between the surface 1118 and the interior surface of the split cover 1104 may be provided, for example, by an adhesive or gasket.

Still further in contrast to other embodiments shown in the present disclosure, there may be no lens above the light emitter 1108 and/or no light filter above the light receiver 1110, because the height and width of the light-blocking wall 1116 may be sufficient to limit what portions of light emitted by the light emitter 1108 are reflected toward the light receiver 1110.

Figure 12:
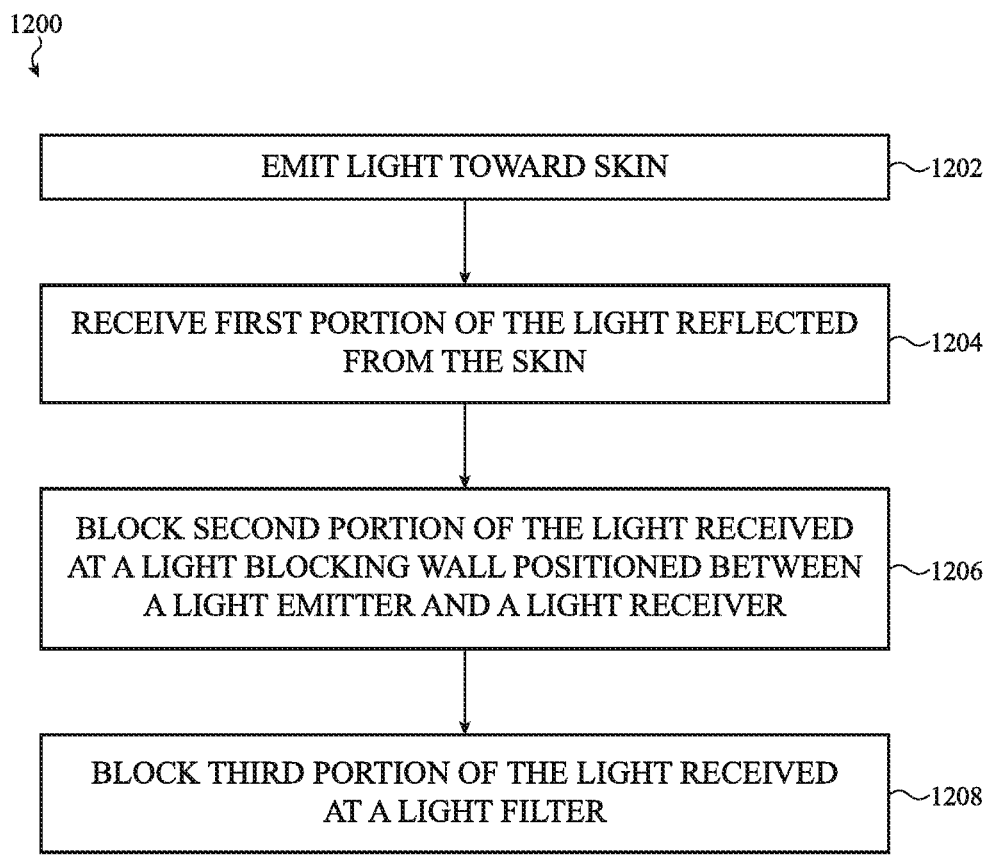
FIG. 12 shows an example method of determining a biological parameter of a user wearing a watch or other wearable electronic device.

FIG. 12 shows an example method 1200 of operation of an optical heart rate detector. The method 1200 may provide data that is used by a processing subsystem of an electronic device to determine a biological parameter of a user wearing a watch or other wearable electronic device, such as a watch or wearable electronic device described herein.

At block 1202, the method includes emitting light from a light emitter within the watch, toward the skin of the user. At least a portion of the light may travel through a cover that forms part of a housing of the watch. The operation(s) at 1202 may be performed, for example, by the light emitter described with reference to FIGS. 2, 4, 5, 6, 9, 10, and 11.

At block 1204, a first portion of the light, reflected from the skin of the user, may be received by a light receiver within the watch. The operation(s) at 1204 may be performed, for example, by the light receiver described with reference to FIGS. 2, 4, 5, 6, 9, 10, and 11.

At block 1206, a second portion of the light may be blocked by a light-blocking wall positioned between the light emitter and the light receiver. The second portion of light may include light that does not travel through the cover or light that reflects from a surface of the cover before passing into the cover. The operation(s) at 1206 may be performed, for example, by the light-blocking wall described with reference to FIGS. 2, 4, 5, 6, 9, 10, and 11.

At block 1208, a third portion of the light may be received at a light filter that is attached to (directly or otherwise) the cover. The third portion of light may be prevented from being received at the light receiver by the light filter. The third portion of light may include light that is reflected toward the light receiver before passing into (or sufficiently into) the skin of the user. The operation(s) at 1208 may be performed, for example, by the light filter described with reference to FIGS. 2-7 and 9-11.

The processing subsystem (and particularly, its processor) of the electronic device may use one or more properties of the light received by the light filter to determine a biological parameter, as discussed above. For example, the amount of light and/or amplitude of light received by the emitter(s) may be used by the processing subsystem to determine a wearer's blood pressure and heart rate.

Figure 13A:
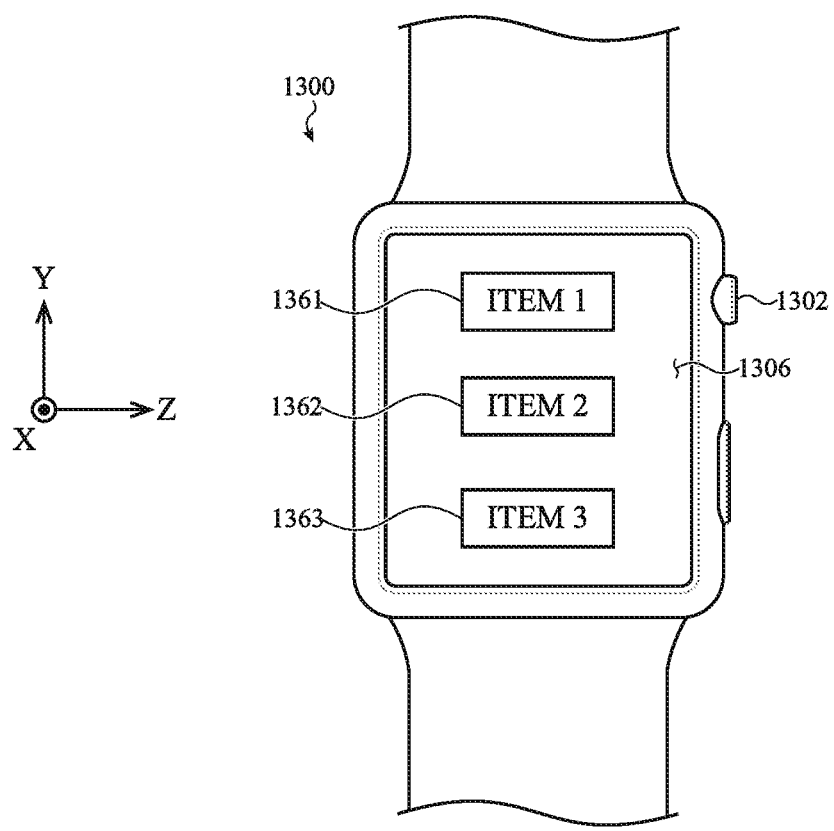
FIGS. 13A-15B generally depict examples of manipulating graphics displayed on an electronic device through inputs provided by force and/or rotational inputs to a crown of the device.
Figure 13B:
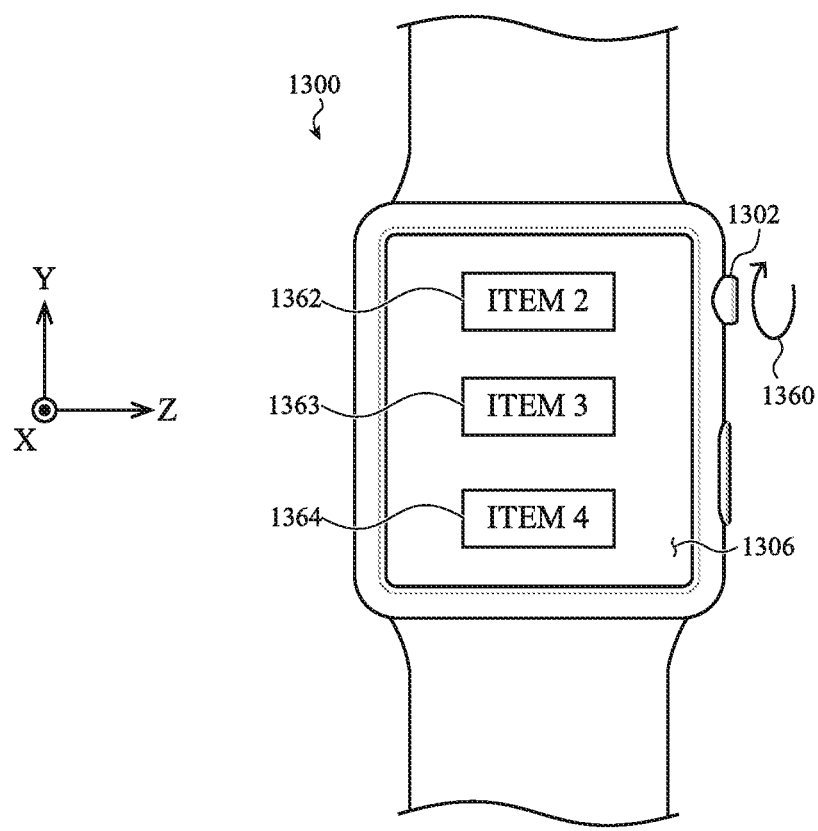

As discussed above, graphics displayed on the electronic devices herein may be manipulated through inputs provided to a crown. FIGS. 13A-13B generally depict examples of changing a graphical output displayed on an electronic device through inputs provided by force and/or rotational inputs to a crown assembly of the device. This manipulation (e.g., selection, acknowledgement, motion, dismissal, magnification, and so on) of a graphic may result in changes in operation of the electronic device and/or graphical output displayed by the electronic device. Although specific examples are provided and discussed, many operations may be performed by rotating and/or applying force to a crown such as the examples described above. Accordingly, the following discussion is by way of example and not limitation.

FIG. 13A depicts an example electronic device 1300 (shown here as an electronic watch) having a crown 1302. The crown 1302 may be similar to the examples described above, and may receive force inputs along a first lateral direction, a second lateral direction, or an axial direction of the crown. The crown 1302 may also receive rotational inputs. A display 1306 provides a graphical output (e.g., shows information and/or other graphics). In some embodiments, the display 1306 may be configured as a touch-sensitive display capable of receiving touch and/or force input. In the current example, the display 1306 depicts a list of various items 1361, 1362, 1363, all of which are example indicia.

FIG. 13B illustrates how the graphical output shown on the display 1306 changes as the crown 1302 rotates, partially or completely (as indicated by the arrow 13). Rotating the crown 1302 causes the list to scroll or otherwise move on the screen, such that the first item 1361 is no longer displayed, the second and third items 1362, 1363 each move upwards on the display, and a fourth item 1364 is now shown at the bottom of the display. This is one example of a scrolling operation that can be executed by rotating the crown 1302. Such scrolling operations may provide a simple and efficient way to depict multiple items relatively quickly and in sequential order. In some examples, the items may be used to trigger various aspects of the optical sensor subsystems described herein, or to select various outputs of the optical sensor subsystems for further review. A speed of the scrolling operation may be controlled by the amount of rotational force applied to the crown 1302 and/or the speed at which the crown 1302 is rotated. Faster or more forceful rotation may yield faster scrolling, while slower or less forceful rotation yields slower scrolling. The crown 1302 may receive an axial force (e.g., a force inward toward the display 1306 or watch body) to select an item from the list, in certain embodiments.

Figure 14A:
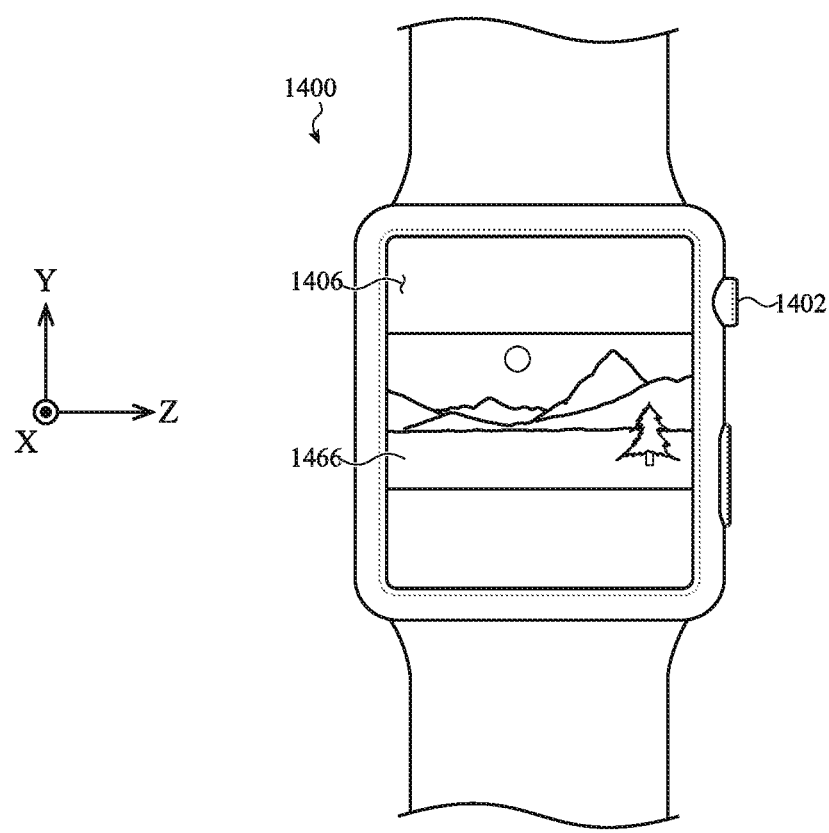
Figure 14B:
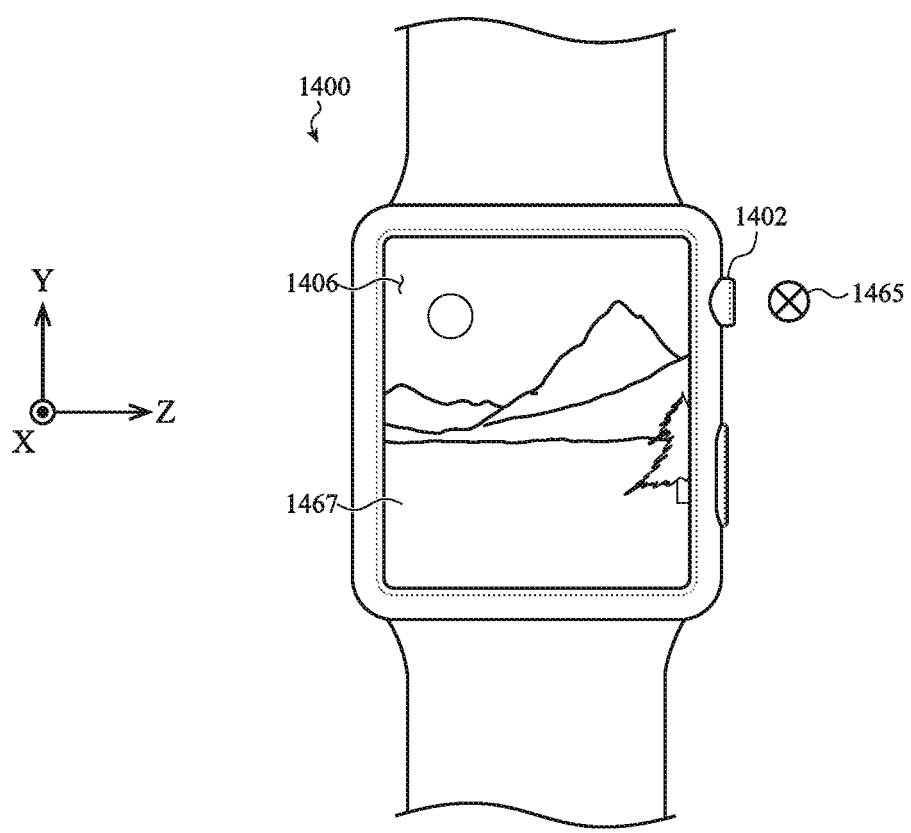

FIGS. 14A and 14B illustrate an example zoom operation. The display 1406 depicts a picture 1466 at a first magnification, shown in FIG. 14A; the picture 1466 is yet another example of an indicium. A user may apply a lateral force (e.g., a force along the x-axis) to the crown 1402 of the electronic device 1400 (illustrated by arrow 1465), and in response the display may zoom into the picture 1466, such that a portion 1467 of the picture is shown at an increased magnification. This is shown in FIG. 14B. The direction of zoom (in vs. out) and speed of zoom, or location of zoom, may be controlled through force applied to the crown 1402, and particularly through the direction of applied force and/or magnitude of applied force. Applying force to the crown 1402 in a first direction may zoom in, while applying force to the crown 1402 in an opposite direction may zoom out. Alternately, rotating or applying force to the crown 1402 in a first direction may change the portion of the picture subject to the zoom effect. In some embodiments, applying an axial force (e.g., a force along the z-axis) to the crown 1402 may toggle between different zoom modes or inputs (e.g., direction of zoom vs. portion of picture subject to zoom). In yet other embodiments, applying force to the crown 1402 along another direction, such as along the y-axis, may return the picture 1466 to the default magnification shown in FIG. 14A.

Figure 15A:
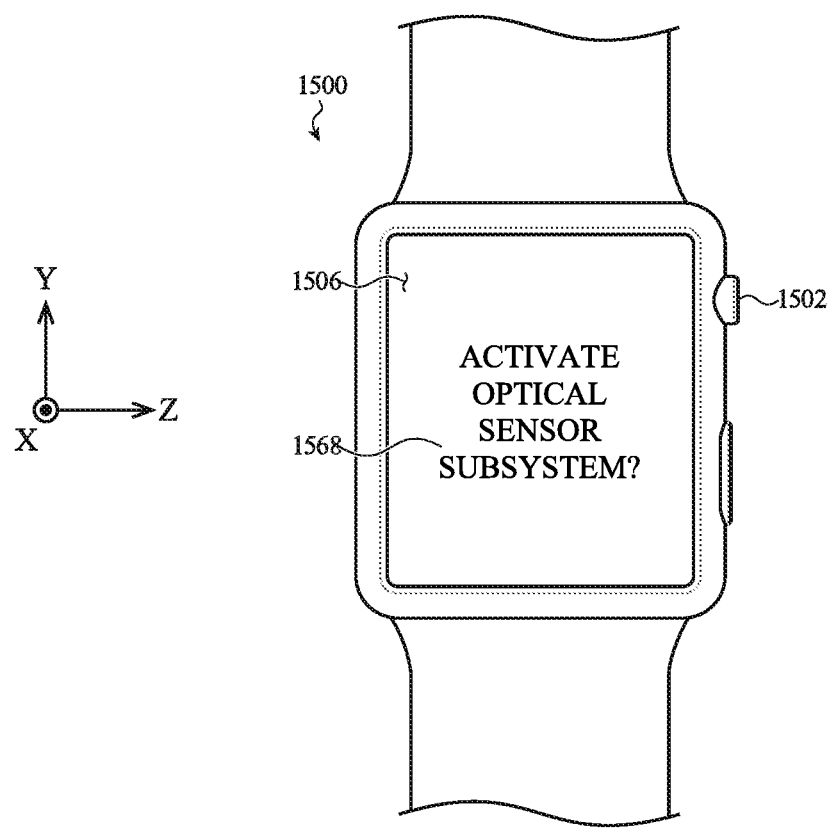
Figure 15B:
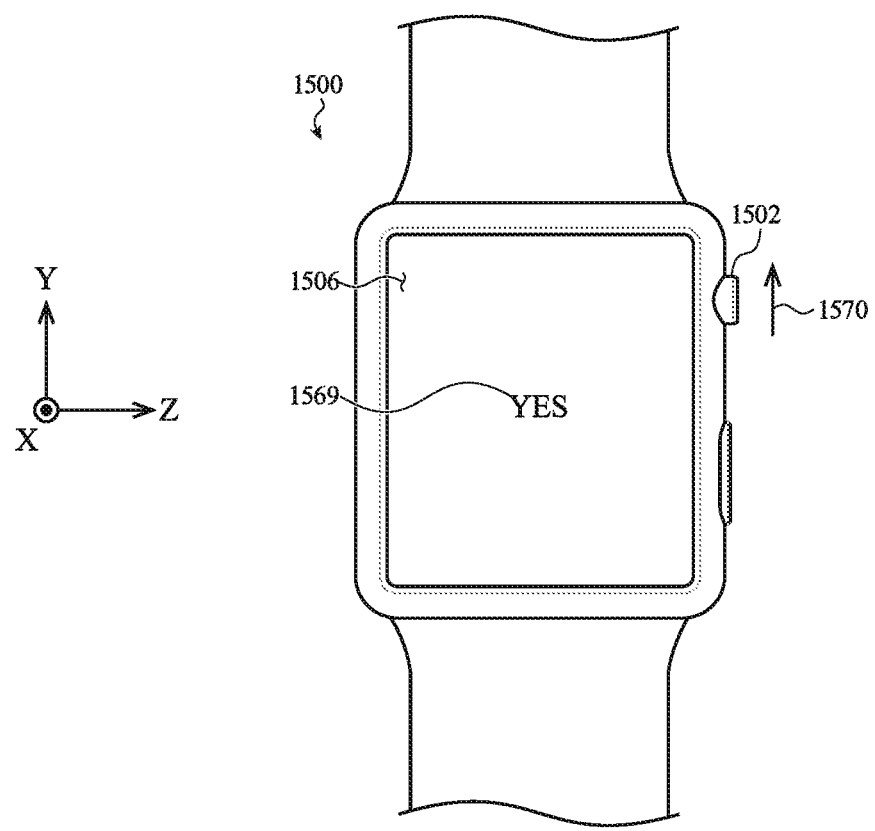

FIGS. 15A and 15B illustrate possible use of the crown 1502 to change an operational state of the electronic device 1500 or otherwise toggle between inputs. Turning first to FIG. 15A, the display 1506 depicts a question 1568, namely, "Activate optical sensor subsystem?" As shown in FIG. 15B, a lateral force may be applied to the crown 1502 (illustrated by arrow 1570) to answer the question. Applying force to the crown 1502 provides an input interpreted by the electronic device 1500 as "yes," and so "YES" is displayed as a graphic 1569 on the display 1506. Applying force to the crown 1502 in an opposite direction may provide a "no" input. Both the question 1568 and graphic 1569 are examples of indicia. As one non-limiting example, a graphic or indicium of a heart rate, blood pressure, or the like may be shown on the display 1506 in response to the user selecting "YES," for example by rotating, translating, or touching the crown 1502.

In the embodiment shown in FIGS. 15A and 15B, the force applied to the crown 1502 is used to directly provide the input, rather than select from options in a list (as discussed above with respect to FIGS. 13A and 13B).

As mentioned previously, force or rotational input to a crown of an electronic device may control many functions beyond those listed here. The crown may receive distinct force or rotational inputs to adjust a volume of an electronic device, a brightness of a display, or other operational parameters of the device. A force or rotational input applied to the crown may rotate to turn a display on or off, or turn the device on or off. A force or rotational input to the crown may launch or terminate an application on the electronic device. Further, combinations of inputs to the crown may likewise initiate or control any of the foregoing functions, as well.

In some cases, the graphical output of a display may be responsive to inputs applied to a touch-sensitive display (e.g., displays 1306, 1406, 1506, and the like) in addition to inputs applied to a crown. The touch-sensitive display may include or be associated with one or more touch and/or force sensors that extend along an output region of a display and which may use any suitable sensing elements and/or sensing techniques to detect touch and/or force inputs applied to the touch-sensitive display. The same or similar graphical output manipulations that are produced in response to inputs applied to the crown may also be produced in response to inputs applied to the touch-sensitive display. For example, a swipe gesture applied to the touch-sensitive display may cause the graphical output to move in a direction corresponding to the swipe gesture. As another example, a tap gesture applied to the touch-sensitive display may cause an item to be selected or activated. In this way, a user may have multiple different ways to interact with and control an electronic watch, and in particular the graphical output of an electronic watch. Further, while the crown may provide overlapping functionality with the touch-sensitive display, using the crown allows for the graphical output of the display to be visible (without being blocked by the finger that is providing the touch input).

Figure 16:
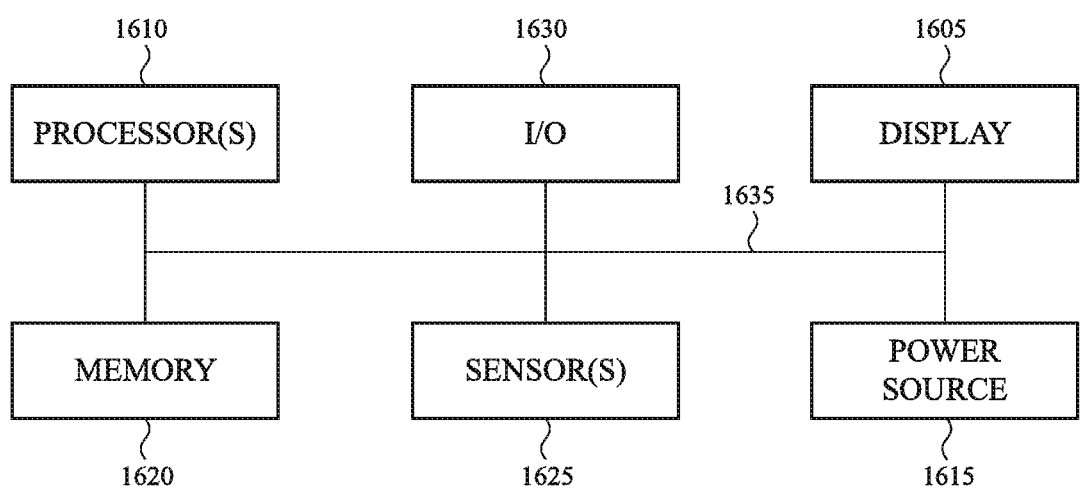
FIG. 16 shows a sample electrical block diagram of an electronic device such as a watch or other suitable electronic device.

FIG. 16 shows a sample electrical block diagram of an electronic device 1600, which electronic device may in some cases take the form of any of the watches or other wearable electronic devices described with reference to FIGS. 1-6, 8-11, and 13A-15B, or other portable or wearable electronic devices. The electronic device 1600 can include a display 1605 (e.g., a light-emitting display), a processor 1610, a power source 1615, a memory 1620 or storage device, a sensor 1625, and an input/output (I/O) mechanism 1630 (e.g., an input/output device, input/output port, or haptic input/output interface). The processor 1610 can control some or all of the operations of the electronic device 1600. The processor 1610 can communicate, either directly or indirectly, with some or all of the components of the electronic device 1600. For example, a system bus or other communication mechanism 1635 can provide communication between the processor 1610, the power source 1615, the memory 1620, the sensor 1625, and the input/output mechanism 1630.

The processor 1610 can be implemented as any electronic device capable of processing, receiving, or transmitting data or instructions. For example, the processor 1610 can be a microprocessor, a central processing unit (CPU), an application-specific integrated circuit (ASIC), a digital signal processor (DSP), or combinations of such devices. As described herein, the term "processor" is meant to encompass a single processor or processing unit, multiple processors, multiple processing units, or other suitably configured computing element or elements.

It should be noted that the components of the electronic device 1600 can be controlled by multiple processors. For example, select components of the electronic device 1600 (e.g., a sensor 1625) may be controlled by a first processor and other components of the electronic device 1600 (e.g., the display 1605) may be controlled by a second processor, where the first and second processors may or may not be in communication with each other.

The power source 1615 can be implemented with any device capable of providing energy to the electronic device 1600. For example, the power source 1615 may be one or more batteries or rechargeable batteries. Additionally or alternatively, the power source 1615 can be a power connector or power cord that connects the electronic device 1600 to another power source, such as a wall outlet.

The memory 1620 can store electronic data that can be used by the electronic device 1600. For example, the memory 1620 can store electrical data or content such as, for example, audio and video files, documents and applications, device settings and user preferences, timing signals, control signals, and data structures or databases. The memory 1620 can be configured as any type of memory. By way of example only, the memory 1620 can be implemented as random access memory, read-only memory, Flash memory, removable memory, other types of storage elements, or combinations of such devices.

The electronic device 1600 may also include one or more sensors 1625 positioned almost anywhere on the electronic device 1600. The sensor(s) 1625 can be configured to sense one or more type of parameters, such as but not limited to, pressure, light, touch, heat, movement, relative motion, biometric data (e.g., biological parameters), and so on. For example, the sensor(s) 1625 may include a heat sensor, a position sensor, a light or optical sensor, an accelerometer, a pressure transducer, a gyroscope, a magnetometer, a health monitoring sensor, and so on. Additionally, the one or more sensors 1625 can utilize any suitable sensing technology, including, but not limited to, capacitive, ultrasonic, resistive, optical, ultrasound, piezoelectric, and thermal sensing technology.

The 110 mechanism 1630 can transmit and/or receive data from a user or another electronic device. An 110 device can include a display, a touch sensing input surface, one or more buttons (e.g., a graphical user interface "home" button), one or more cameras, one or more microphones or speakers, one or more ports such as a microphone port, and/or a keyboard. Additionally or alternatively, an 110 device or port can transmit electronic signals via a communications network, such as a wireless and/or wired network connection. Examples of wireless and wired network connections include, but are not limited to, cellular, Wi-Fi, Bluetooth, IR, and Ethernet connections.

As described above, one aspect of the present technology is the gathering and use of data available from various sources, including the gathering and use of biological parameters of a user (or data indicative of, or facilitating determining, a biological parameter), to monitor or improve the user's health or fitness. The present disclosure contemplates that in some instances, this gathered data may include personal information data that uniquely identifies a specific person, or can be used to contact, locate, or identify a specific person. Such personal information data can include demographic data, location-based data, telephone numbers, email addresses, twitter ID's, home addresses, data or records relating to a user's health or level of fitness (e.g., vital sign measurements, medication information, exercise information), date of birth, or any other identifying or personal information.

The present disclosure recognizes that the use of such personal information data, in the present technology, can be used to the benefit of users. For example, the personal information data can be used to aid a user in monitoring or improving their health or fitness (e.g., biological parameters or health and fitness data may be used to provide insights into a user's general wellness, or may be used as positive feedback to individuals using technology to pursue wellness goals).

The present disclosure contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining personal information data private and secure. Such policies should be easily accessible by users, and should be updated as the collection and/or use of data changes. Personal information from users should be collected for legitimate and reasonable uses of the entity and not shared or sold outside of those legitimate uses. Further, such collection/sharing should occur after receiving the informed consent of the users. Additionally, such entities should consider taking any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices. In addition, policies and practices should be adapted for the particular types of personal information data being collected and/or accessed and adapted to applicable laws and standards, including jurisdiction-specific considerations. For instance, in the US, collection of or access to certain health data may be governed by federal and/or state laws, such as the Health Insurance Portability and Accountability Act (HIPAA); whereas health data in other countries may be subject to other regulations and policies and should be handled accordingly. Hence different privacy practices should be maintained for different personal data types in each country.

Despite the foregoing, the present disclosure also contemplates embodiments in which users selectively block the use of, or access to, personal information data. That is, the present disclosure contemplates that hardware and/or software elements can be provided to prevent or block access to such personal information data. For example, in the case of biological parameters or conditions identified therefrom, the present technology can be configured to allow users to select to "opt in" or "opt out" of participation in the collection of personal information data during registration for services or anytime thereafter. In another example, users can select not to provide health or fitness-associated data to the providers of applications or services, or can prevent the transmission of such data from the device on which it is collected or outside a collection of devices that are personal to a user from which the data is obtained. In yet another example, a user can select to limit the length of time health or fitness data, or biological parameters from which such data is derived, is maintained. In addition to providing "opt in" and "opt out" options, the present disclosure contemplates providing notifications relating to the access or use of personal information. For instance, a user may be notified upon downloading an app that their personal information data will be accessed and then reminded again just before personal information data is accessed by the app.

Moreover, it is the intent of the present disclosure that personal information data should be managed and handled in a way to minimize risks of unintentional or unauthorized access or use. Risk can be minimized by limiting the collection of data and deleting data once it is no longer needed. In addition, and when applicable, including in certain health related applications, data de-identification can be used to protect a user's privacy. De-identification may be facilitated, when appropriate, by removing specific identifiers (e.g., date of birth, etc.), controlling the amount or specificity of data stored (e.g., collecting location data at a city level rather than at an address level), controlling how data is stored (e.g., aggregating data across users), and/or other methods.

Therefore, although the present disclosure broadly covers use of personal information data to implement one or more various disclosed embodiments, the present disclosure also contemplates that the various embodiments can also be implemented without the need for accessing at least some personal information data. That is, the various embodiments of the present technology are not rendered inoperable due to the lack of a portion of such personal information data. For example, biological parameters can be ascertained or stored without associating the biological parameters with information identifying a particular user from which they are obtained, or with a bare minimum amount of personal information, such as non-personal information already available to service providers or publicly available information.

The foregoing description, for purposes of explanation, uses specific nomenclature to provide a thorough understanding of the described embodiments. However, it will be apparent to one skilled in the art that the specific details are not required in order to practice the described embodiments. Thus, the foregoing descriptions of the specific embodiments described herein are presented for purposes of illustration and description. They are not targeted to be exhaustive or to limit the embodiments to the precise forms disclosed. It will be apparent to one of ordinary skill in the art that many modifications and variations are possible in view of the above teachings.

What is claimed is:

1. An electronic watch, comprising:
    a housing defining a peripheral side of the electronic watch;
    a backside housing member coupled to the housing, the backside housing member defining a first portion of a back side of the electronic watch and a first hole extending through the backside housing member;
    a sensor subassembly positioned in the first hole and comprising:
        a cover formed of a unitary piece of a transparent material and attached to the backside housing member, the cover having a convex exterior surface defining second portion of the back side of the electronic watch and an interior surface opposite the exterior side;
        a first electrode having a first exterior portion extending along a first portion of the convex exterior surface of the cover, a first interior portion extending along a first portion of the interior surface of the cover, and a first edge portion electrically coupling the first exterior portion and the first interior portion and positioned along an edge surface of the cover;
        a second electrode, different from the first electrode, having a second exterior portion extending along a second portion of the convex exterior surface of the cover, a second interior portion extending along a second portion of the interior surface of the cover, and a second edge portion electrically coupling the second exterior portion and the second interior portion and positioned along the edge surface of the cover, wherein the first portion of the convex exterior surface of the cover and the first portion of the interior surface of the cover are different from the second portion of the convex exterior surface of the cover and the second portion of the interior surface of the cover, respectively;
        a substrate;
        a first light-blocking wall at least partially surrounding a central region of the sensor subassembly;
        a second light-blocking wall extending at least partially around the first light-blocking wall to define, between the first light-blocking wall and the second light-blocking wall, a peripheral region of the sensor subassembly;
        a set of light emitters positioned on the substrate and configured to emit light through the cover;
        a set of photodetectors positioned on the substrate and configured to receive a reflected portion of the light through the cover; and
        a processor conductively coupled to the set of light emitters and the set of photodetectors and configured to determine a biological parameter using the reflected portion of the light, and conductively coupled to the first electrode via the first interior portion and to the second electrode via the second interior portion and configured to determine an electrocardiograph using signals from the first and second electrodes;
    a printed circuit board defining a second hole; and
    a magnet positioned in the second hole and attached to the substrate.

2. The electronic watch of claim 1, wherein:
    the biological parameter is a heart rate;
    the electronic watch further comprises an opaque mask defining a first aperture over the central region of the sensor subassembly and a second aperture over the peripheral region of the sensor subassembly;
    the first aperture and the second aperture are positioned between the first electrode and the second electrode;
    the set of light emitters comprises:
        a first set of light emitters configured to emit light having a first wavelength; and
        a second set of light emitters configured to emit light having a second wavelength;
    the electronic watch further comprises a lens aligned with the first aperture;
    the electronic watch further comprises a light filter comprising a light control film covering the second aperture; and
    the first light-blocking wall prevents at least one of the set of photodetectors from receiving a non-reflected portion of the light.

3. The electronic watch of claim 1, further comprising a magnetic shield attached to the magnet and configured to direct magnetic flux associated with the magnet through the cover.

4. The electronic watch of claim 1, further comprising:
    a display at least partially within the housing; and a crown extending through the housing and configured to provide an input; wherein:
the biological parameter is a heart rate; and
the display is configured to display a graphic of the heart rate in response to the input.

5. The electronic watch of claim 1, further comprising:
a crown extending through the housing; and
a display at least partially positioned in the housing; wherein:
the crown is configured to rotate and translate;
the display shows a graphic; and
the display is configured to change the graphic in response to at least one of the crown rotating or translating.

6. The electronic watch of claim 1, further comprising:
a crown extending through the housing and configured to provide an input; wherein
the set of light emitters is configured to emit the light through the cover in response to the input.

7. The electronic watch of claim 1, wherein:
the first electrode is a first arc-shaped electrode at least partially encircling the peripheral region of the sensor subassembly; and
the second electrode is a second arc-shaped electrode at least partially encircling the peripheral region of the sensor subassembly.

8. The electronic watch of claim 1, wherein the first electrode and the second electrode are electrically insulated from the backside housing member by a non-conductive material.

9. The electronic watch of claim 8, wherein the non-conductive material is a non-conductive adhesive.

10. The electronic watch of claim 2, wherein the light filter at least partially overlaps the opaque mask.

11. The electronic watch of claim 2, wherein the first light-blocking wall and the second light-blocking wall are positioned below the opaque mask.

12. An electronic device, comprising:
a housing formed from a conductive material and defining a peripheral side of the electronic device;
a backside housing member coupled to the housing, the backside housing member defining a first portion of a back side of the electronic device and a first hole extending through the backside housing member;
a sensor subassembly positioned in the first hole and comprising:
  a cover formed of a unitary piece of a transparent material and attached to the backside housing member, the cover defining:
    a first surface interior to the electronic device; and
    a convex second surface exterior to the electronic device;
  a first electrode having a first exterior portion extending along a first portion of the convex second surface of the cover, a first interior portion extending along a first portion of the first surface of the cover, and a first edge portion electrically coupling the first exterior portion and the first interior portion and positioned along an edge surface of the cover;
  a second electrode, different from the first electrode, having a second exterior portion extending along a second portion of the convex second surface of the cover different from the first portion of the convex second surface of the cover, a second interior portion extending along a second portion of the first surface of the cover different from the first portion of the first surface of the cover, and a second edge portion electrically coupling the second exterior portion and the second interior portion and positioned along the edge surface of the cover;
  a substrate;
  a first light-blocking wall at least partially surrounding a central region of the sensor subassembly and attached to the cover along the first surface of the cover and to a first surface of the substrate to attach the substrate to the cover;
  a second light-blocking wall extending at least partially around the first light-blocking wall to define, between the first light-blocking wall and the second light-blocking wall, a peripheral region of the sensor subassembly, the second light-blocking wall attached to the cover along the first surface of the cover and to the first surface of the substrate to attach the substrate to the cover;
  a light emitter attached to the substrate in the central region of the sensor subassembly;
  a photodetector attached to the substrate in the peripheral region of the optical sensor subassembly and configured to receive light emitted by the light emitter and reflected from a medium adjacent the second surface of the cover; and
  a processor operationally connected to the photodetector and configured to determine a heart rate from the light received by the photodetector;
a printed circuit board defining a second hole; and
a magnet positioned in the second hole and attached to the substrate.

13. The electronic device of claim 12, further comprising a crown configured to rotate and translate; wherein the processor is configured to determine the heart rate in response to at least one of the crown rotating or translating.

14. The electronic device of claim 12, wherein:
the first light-blocking wall is a first circular wall; and
the second light-blocking wall is a second circular wall.

15. The electronic device of claim 12, wherein:
the photodetector is one of a set of photodetectors; and
the set of photodetectors is attached to the substrate and defines a radial array of light emitters.

16. The electronic device of claim 12, wherein the optical sensor subassembly comprises:
a set of light emitters including the light emitter; and
a set of photodetectors including the photodetector; wherein
the light emitter is configured to emit light having a first wavelength; and
a second light emitter of the set of light emitters is configured to emit light having a second wavelength that differs from the first wavelength; and
the set of photodetectors are attached to the substrate and positioned in a radial array.

17. A wearable electronic device, comprising:
a housing defining:
  a peripheral side surface of the wearable electronic device;
  a first opening along a front portion of the housing; and
  a second opening along a rear portion of the housing;
a frontside housing member positioned in the front opening of the housing and defining a front surface of the wearable electronic device;
a backside housing member positioned in the second opening and defining a first portion of a back surface of the wearable electronic device and a first hole extending through the backside housing member;
a sensor subassembly positioned in the first hole and comprising:

a cover formed of a unitary piece of a transparent material and attached to the backside housing member, the cover having a convex exterior surface and an interior surface opposite the convex exterior surface;

a first electrode wrapped around a peripheral edge of the cover and defining:
  a first exterior portion extending along a first portion of the convex exterior surface of the cover; and
  a first interior portion extending along a first portion of the interior surface of the cover;

a second electrode, different from the first electrode, wrapped around the peripheral edge of the cover and defining:
  a second exterior portion extending along a second portion of the convex exterior surface of the cover, the second portion of the convex exterior surface different from the first portion of the convex exterior surface; and
  a second interior portion extending along a second portion of the interior surface of the cover, the second portion of the interior surface of the cover different from the first portion of the interior surface of the cover;

an opaque mask on the interior side of the cover, the opaque mask defining a first aperture and a second aperture that are each located between the first electrode and the second electrode;

a substrate;

a first light-blocking wall at least partially surrounding a central region of the sensor subassembly and attached to a first portion of the opaque mask on the interior side of the cover and to a first surface of the substrate to attach the substrate to the cover;

a second light-blocking wall extending at least partially around the first light-blocking wall to define, between the first light-blocking wall and the second light-blocking wall, a peripheral region of the sensor subassembly, the second light-blocking wall attached to a second portion of the opaque mask on the interior side of the cover and to the first surface of the substrate to attach the substrate to the cover;

a light emitter positioned on the substrate and in the central region of the sensor subassembly and configured to emit light through the cover;

a photodetector positioned on the substrate and in the peripheral region of the sensor subassembly and configured to receive a reflected portion of the light through the cover; and a processor coupled to the substrate and conductively coupled to the light emitter and the photodetector and configured to determine a biological parameter using the reflected portion of the light;

a printed circuit board defining a second hole; and a magnet positioned in the second hole and attached to the substrate.

18. The wearable electronic device of claim 17, wherein the first electrode and the second electrode are electrically insulated from the backside housing member.

19. The wearable electronic device of claim 17, wherein:
the photodetector is positioned below the first aperture in the opaque mask; and
the wearable electronic device further includes a light filter attached to the cover in the first aperture.

20. The wearable electronic device of claim 17, wherein:
the light emitter is positioned below the second aperture in the opaque mask; and
the wearable electronic device further includes a lens attached to the cover in the second aperture.

* * * * *